(12) United States Patent
Wang et al.

(10) Patent No.: US 11,040,085 B2
(45) Date of Patent: Jun. 22, 2021

(54) PHARMACEUTICAL COMPOSITION CONTAINING F1 POLYPEPTIDE AND/OR F3 POLYPEPTIDE AND USE THEREOF

(71) Applicants: Tian-Fang Wang, Hefei (CN);
Guo-Ying Ni, Tangshan (CN);
Xiao-Song Liu, Brisbane (AU)

(72) Inventors: Tian-Fang Wang, Hefei (CN);
Guo-Ying Ni, Tangshan (CN);
Xiao-Song Liu, Brisbane (AU)

( * ) Notice: Subject to any disclaimer, the term of this patent is extended or adjusted under 35 U.S.C. 154(b) by 31 days.

(21) Appl. No.: 16/455,609

(22) Filed: Jun. 27, 2019

(65) Prior Publication Data
US 2019/0374603 A1 Dec. 12, 2019

Related U.S. Application Data

(63) Continuation-in-part of application No. PCT/CN2017/000744, filed on Dec. 22, 2017.

(30) Foreign Application Priority Data

Dec. 27, 2016 (CN) .......................... 201611223048.4

(51) Int. Cl.
| | |
|---|---|
| *A61K 38/00* | (2006.01) |
| *A61K 38/16* | (2006.01) |
| *A61K 38/17* | (2006.01) |
| *A61P 35/00* | (2006.01) |
| *A61K 31/4745* | (2006.01) |
| *A61K 39/12* | (2006.01) |
| *A61K 39/00* | (2006.01) |

(52) U.S. Cl.
CPC ...... *A61K 38/1703* (2013.01); *A61K 31/4745* (2013.01); *A61K 39/12* (2013.01); *A61P 35/00* (2018.01); *A61K 2039/585* (2013.01)

(58) Field of Classification Search
None
See application file for complete search history.

(56) References Cited

FOREIGN PATENT DOCUMENTS

| CN | 1363558 | 8/2002 |
|---|---|---|
| WO | WO9213881 | 8/1992 |
| WO | WO9527728 | 10/1995 |

OTHER PUBLICATIONS

Apponyi et al. Host-defence peptides of Australian anurans: structure, mechanism of action and evolutionary significance. Peptides 25 (2004) 1035-1054.*
Yuan et al. Genital warts treatment: Beyond imiquimod. Human Vaccines & Immunotherapeutics, 2018, vol. 14, No. 7, 1815-1819.*
Zaiou, M. Multifunctional antimicrobial peptides: therapeutic targets in several human diseases. J Mol Med (2007) 85:317-329.*
International Search Report of PCT/CN2017/000744.
New antibiotic Caerin 1 Peptides from the skin secretion of the Australian tree frog Litoria Chloris. Comparison of the activities of the Caerin 1 Peptides from the genus *Litoria*, Simon T. Stejnborner, et al., J. Peptide Res. 31 Dec. 1998, vol. 25, pp. 121-126.
Host-defence peptides of Australian anurans: structure, mechanism of action and evolutionary significance, Margit A. Appony, et. al., Peptides. May 10, 2004, vol. 25, pp. 1035-1054.

* cited by examiner

*Primary Examiner* — Nianxiang Zou

(57) ABSTRACT

A pharmaceutical composition containing F1 polypeptide and/or F3 polypeptide and a use thereof are provided. The pharmaceutical composition is made into a common dosage form, such as an emulsion and an ointment, and used for treating a disease, such as a wart associated with a HPV infection, or a solid tumor associated with or not associated with the HPV infection.

13 Claims, 22 Drawing Sheets

Specification includes a Sequence Listing.

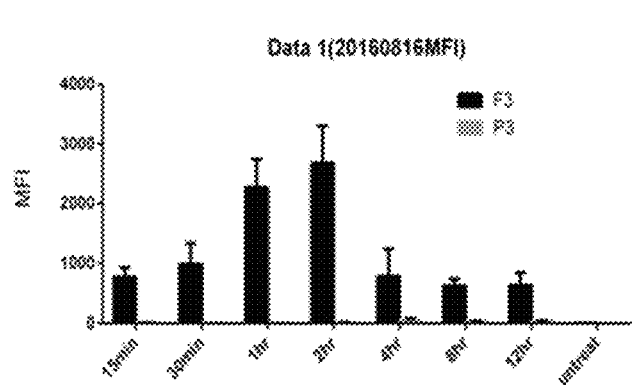
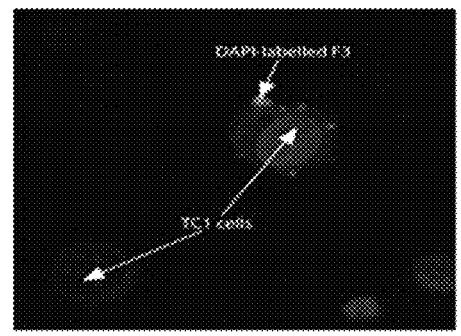
FIG. 5A        FIG. 5B
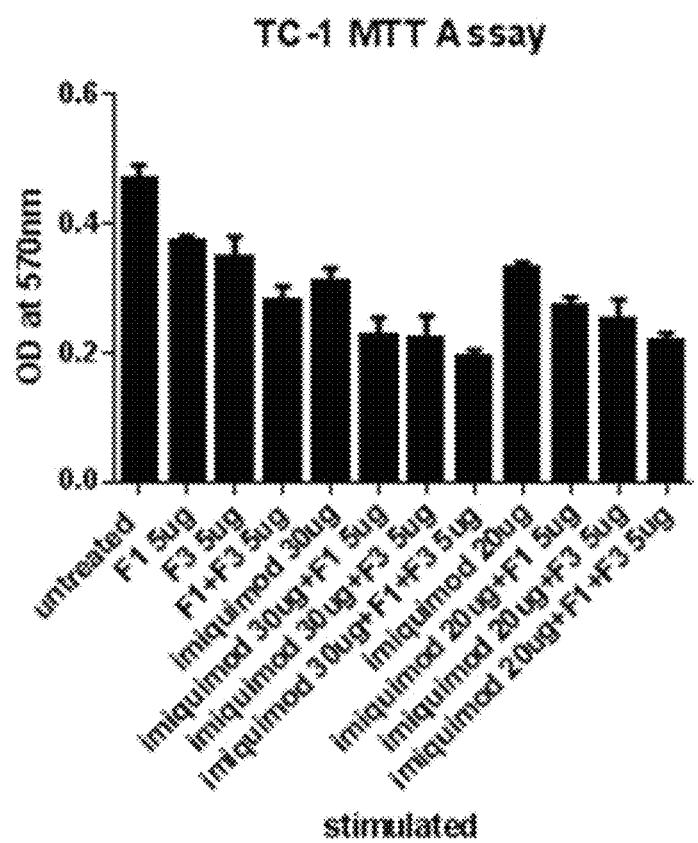
FIG. 6

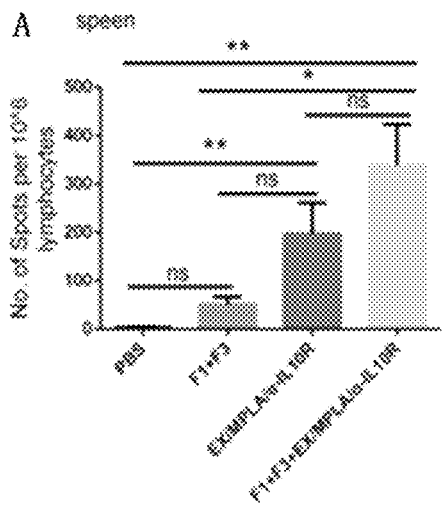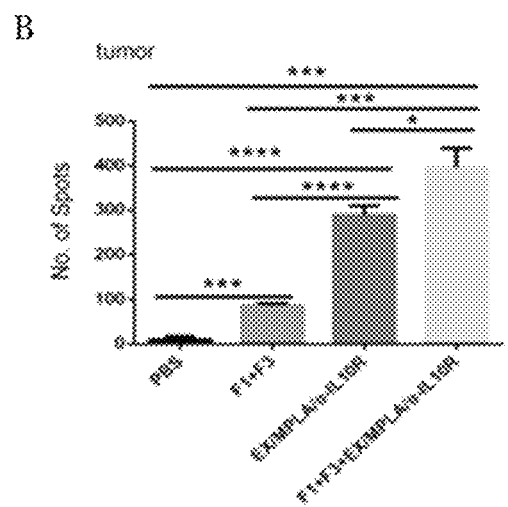
FIG. 15A  FIG. 15B
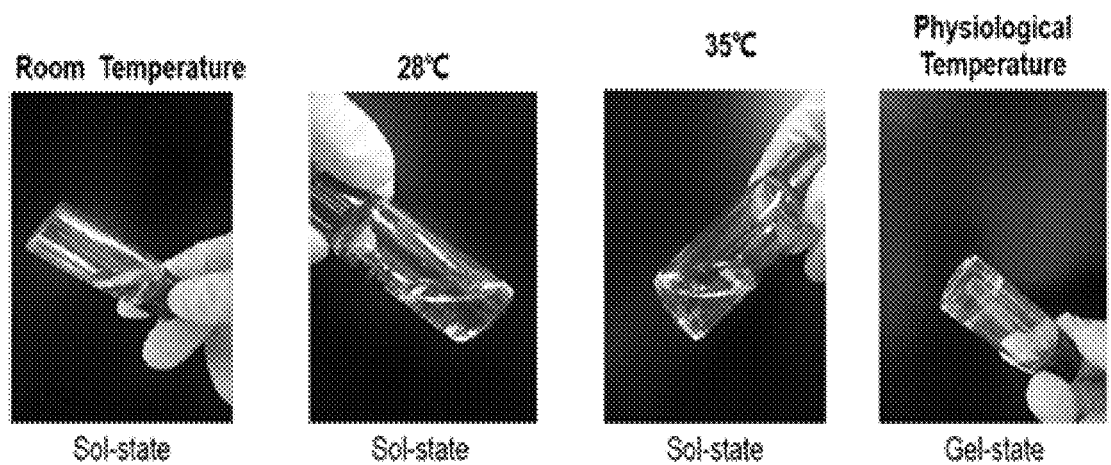
FIG. 16A  FIG. 16B  FIG. 16C  FIG. 16D

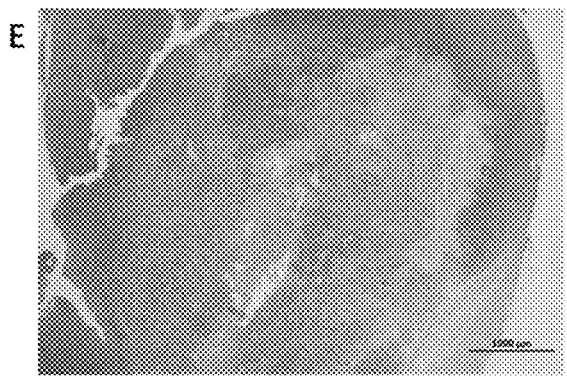
Imiquimod+F1/F3 gel
FIG. 21E
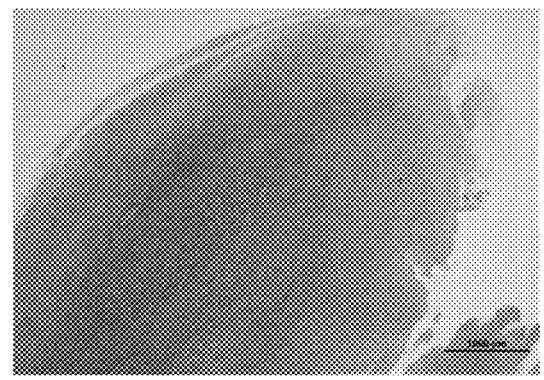
Gel only
FIG. 21F
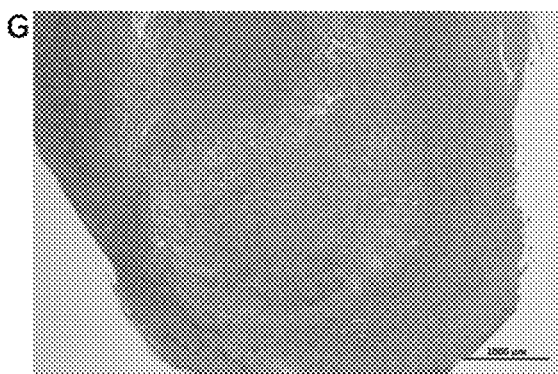
Imiquimod+Gel only
FIG. 21G
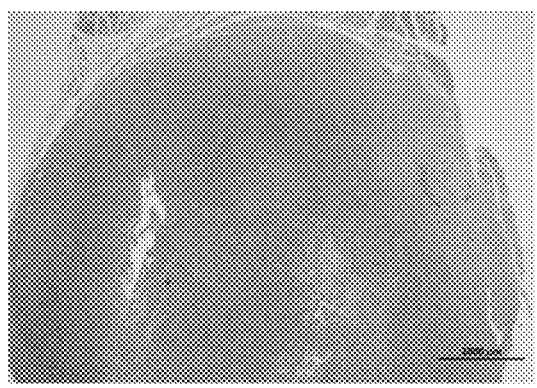
P3 gel
FIG. 21H
FIG. 21

PHARMACEUTICAL COMPOSITION CONTAINING F1 POLYPEPTIDE AND/OR F3 POLYPEPTIDE AND USE THEREOF

CROSS-REFERENCE TO RELATED APPLICATIONS

This application claims all benefits accruing under 35 U.S.C. § 119 from China Patent Application No. 201611223048.4, filed on Dec. 27, 2016 in the State Intellectual Property Office of China, the content of which is hereby incorporated by reference. This application is a continuation-in-part under 35 U.S.C. § 120 of international patent application PCT/CN2017/000744 filed on Dec. 22, 2017, the content of which is also hereby incorporated by reference.

SEQUENCE LISTING

This application contains a Sequence Listing in computer readable form. The computer readable form is incorporated herein by reference. The name of the ASCII text file is 134-JBP198711264US-SequenceListing-20210319, which was created on Mar. 19, 2021, and has a size of 1068 bytes.

TECHNICAL FIELD

The present disclosure relates to the technical field of pharmaceutical preparations of polypeptides, and more specifically to pharmaceutical compositions containing F1 polypeptide and/or F3 polypeptide and use thereof.

BACKGROUND

A variety of diseases can be caused by a human papillomavirus (HPV) infection, such as cervical cancer, vulvar cancer, penile cancer, anal cancer, oral cancer, and some head and neck cancers. The cervical cancer, which is closely related to a persistent infection of HPV, especially HPV-16 and HPV-18, is one with malignant tumors and is the second most common cancer in females. Although a vaccine for preventing HPV infection has been applied from 2006, such vaccine is ineffective for current infections of HPV and the diseases caused therefrom since the vaccine is only appropriate for healthy individuals uninfected by HPV. At present, there are still about 500,000 new cases of the cervical cancer, and about 200,000 women die from this disease each year worldwide. China now has 400,000 cervical cancer patients with a mortality up to 11.3%. In addition, vulvar cancer, penile cancer, anal cancer, and oral cancer are also common malignant tumors in clinic.

Besides, the HPV infection can also cause pathological changes in respiratory tract and reproductive organ, such as condyloma acuminate, which is a common sexually transmitted disease, and recurrent respiratory papillomatosis, which is a rare disease, more common in newborns and children, and sometimes life-threatening. The two diseases are usually caused by HPV-6 or HPV-11 infection.

The condyloma acuminate is a sexually transmitted disease and spread mainly by an unclean sexual intercourse. The condyloma acuminate is one of the most common sexually transmitted disease and about 1% of sexually active population suffer from this disease. One clinical manifestation of the condyloma acuminate is verrucosa neoplasms on the reproductive organ or anus, which is persistently infected and recurrent for some patients after treatment. Human cellular immunity to HPV is an important immunologic mechanism to control the condyloma acuminate. For the patients with immune deficiencies, the condyloma acuminate frequently occurs, intractable, and refractory. The number of condyloma acuminate patients have occupied a lot of medical resources and affected the social stability.

Currently there is no method capable of permanently curing the condyloma acuminate. The wart body can be removed by a physical or chemical method, such as freezing, laser ablation, and the like. However, it is difficult to remove the condyloma body completely by such method and relapse of the condyloma acuminate is easy. Immunotherapy, such as local injection of interferon α to the condyloma body, is used to treat the condyloma acuminate. Nonspecific immunotherapy is also partially effective to treat the condyloma acuminate.

An internationally accepted and the most effective method to treat the condyloma acuminate currently is topical application of 5% of Imiquimod emulsion, which has 50% to 70% of effective rate and about 10% of recurrence rate.

Head and neck squamous cell carcinoma (HNSCC) is the $6^{th}$ most common cancer worldwide, with nearly 600,000 people diagnosed every year, and more than 300,000 deaths. HNSCC is often associated with tobacco and alcohol use and with poor oral hygiene. HNSCCs are not uncommon, for example, according to GLOBOCAN 2012, the estimated age standardized incidence rate in China is 2.7 per 100,000, and a recent report, based on oropharyngeal cancer (OPC) reported to 135 cancer registries during 2008-2012, estimated the age-standardized incidence of OPC as 2.22/100,000 person-years using the 2000 Chinese standard population (ASRIC and ASRMC) and 0.94/100,000 person-years using the 1985 Segi's world standard population (ASRIW and ASRMW).

Over the past decade, there has been a shift in the primary site distribution of HNSCC in western countries, with a steady increase in OPC and a decline in the cancers of the larynx and hypopharynx. Persisting infection of the oropharynx and tonsil with HPV-16 is associated with a subset of OPC that are of lower average age at onset, and are not strongly associated with alcohol and tobacco use. HPV associated OPC respond better to chemoradiotherapy than HPV negative OPC, and in the majority of studies, HPV associated OPC have a better survival compared with stage matched HPV negative OPC.

Melanoma and nonmelanoma skin cancer (NMSC) are now the most common types of cancer in white populations. Cutaneous malignant melanoma is the most rapidly increasing cancer in white populations. The frequency of its occurrence is closely associated with the constitutive colour of the skin and depends on the geographical zone. The highest incidence rates have been reported from Queensland, Australia with 56 new cases per year per 100,000 for men and 43 for women.

Sequences of the F1 polypeptide and the F3 polypeptide were firstly published in the article S. T. Steinborner, et al., J. Pept. Res., 1998, 51, 121, page 4. The sequence of the F1 polypeptide is SEQ ID NO: 1 and the sequence of the F3 polypeptide is SEQ ID NO: 2.

The article M. A. Apponyi, et al., Peptides, 2004, 25, 1035 further disclosed that the F1 has inhibiting effect on tumor. There is no report about effect of the F3 on tumor, effects of the F1 and the F3 on treating the condyloma acuminate, or a superimposed effect of the two polypeptides.

Therefore, there is a need now to develop a drug having a short treatment course, less dosage of active components, obvious curative effect, low recurrence rate, slight side effect, and low treatment cost.

SUMMARY

In one aspect, a method for preparing a F1 polypeptide or a F3 polypeptide is provided, comprising the steps of:

1) firstly inducing a tree frog to secrete a thick liquid with a white appearance by stimulating the tree frog with a direct current having a voltage of 5 volts to 15 volts;

2) collecting the liquid and transferring the liquid into an aqueous solution containing 15 wt % to 30 wt % alcohol, preferably 20 wt % methanol or ethanol, and vibrating and then filtering through a PVDF membrane having a pore diameter of 0.45 μm;

3) filtering a clear liquid out, and drying the clear liquid in a low temperature vacuum centrifugal dryer to form a white solid powder;

4) dissolving the white solid powder into a solution having 0.1 wt % trifluoroacetic acid, and analyzing a sequence of the peptide therein and a post-translational modification possessed by the peptide by a high performance liquid chromatography tandem mass spectrometry;

5) synthesizing the F1 polypeptide or the F3 polypeptide respectively by employing a solid phase peptide synthesis according to the sequence of the peptide and the post-translational modification analyzed, specifically comprising the steps of:

a) on a CS336X peptide synthesizer, with a chloromethyl polystyrene resin as an insoluble solid state carrier, covalently attaching a C-terminal amino acid of the F1 polypeptide or the F3 polypeptide (an amino acid with its amino protected by a blocking group) to the solid state carrier;

b) removing the protecting group of the amino under an action of trifluoroacetic acid, so that a first amino acid is attached to the solid state carrier;

c) activating a carboxyl of a second amino acid having a blocked amino by N,N'-dicyclohexylcarbodiimide, (DCC, dicyclohexylcarbodiimide), and then causing the second amino acid having its carboxyl activated by DCC to react with the amino of the first amino acid attached to the solid state carrier to form a peptide bond, so that a dipeptide with a protecting group is produced on the solid state carrier;

d) repeating the above peptide forming reaction to cause a peptide chain to grow from C-terminal to N-terminal until achieving a required chain length, finally removing the protecting group, and performing a deprotection and depolymerization for the resin spontaneously in a solution of TFA/DCM/$H_2O$/TIPS with a volume ratio of 90:5:2.5:2.5;

d) precipitating with 10 equivalents of cold either and purifying by reversed-phase high-performance liquid chromatography to obtain the F1 polypeptide or the F3 polypeptide.

Particularly, in the synthetic process, carboxyls on side chains of glutamic acid and serine are protected by t-butyl (t-Bu), and a side chain of histidine is protected by t-butyloxy carbonyl (Boc) group to prevent a racemization of the histidine, wherein TFA is an English abbreviation for the trifluoroacetic acid.

The polypeptide prepared by this method has a high purity, and this preparing method is easy to operate and has a low cost.

The present disclosure further provides a first pharmaceutical composition, comprising any one of the F1 polypeptide and the F3 polypeptide or a mixture of the F1 polypeptide and the F3 polypeptide in any proportion, and a pharmaceutically acceptable excipient.

In one embodiment, the pharmaceutical composition is prepared as an injection liquid for intravenous injection, intramuscular injection, or hypodermic injection suitable for parenteral administration or as an emulsion or an ointment suitable for percutaneous administration, such as the emulsion or the ointment.

In one embodiment, a dose of the pharmaceutical composition comprises 3 μg to 30 μg, such as 5 μg to 20 μg, of the F1 polypeptide, the F3 polypeptide, or a mixture thereof when used for tumor bearing mice.

The present disclosure further provides a second pharmaceutical composition further comprising Imiquimod. The pharmaceutical composition is prepared as an injection liquid for intravenous injection, intramuscular injection, or hypodermic injection suitable for parenteral administration or as an emulsion or an ointment suitable for percutaneous administration, such as the emulsion or the ointment.

A mechanism of the second pharmaceutical composition is that a combination of the F1 polypeptide and the F3 polypeptide induces apoptosis of HPV infected cells to release more viral antigens to be captured by antigen presenting cells, and then induces stronger specific immunity response by the nonspecific immune stimulation of Imiquimod, so as to achieve a curative effect which is unachievable by using Imiquimod or the F1 polypeptide and the F3 polypeptide alone.

Wherein Imiquimod is a nonspecific immunomodulator which activates the nonspecific immunity response by stimulating Toll-like receptors 7/8 so as to activate specific T-cell response to kill the virus infected cells and directly induce apoptosis of cells infected by HPV-6 and HPV-11 to achieve the curative effect.

The present disclosure provides a use of the first pharmaceutical composition in preparation of a drug for preventing and/or treating a disease caused by a HPV infection, wherein the disease is a wart or a solid tumor, the wart is preferably condyloma acuminate, and the solid tumor comprises, but is not limited to, cervical cancer, vulvar cancer, penile cancer, anal cancer, and oral cancer.

The present disclosure provides a use of the second pharmaceutical composition in preparation of a drug for preventing and/or treating a disease caused by a HPV infection, wherein the disease is a wart or a solid tumor, the wart is preferably condyloma acuminate, and the solid tumor comprises, but is not limited to, cervical cancer, vulvar cancer, penile cancer, anal cancer, and oral cancer.

The present disclosure provides a use of the second pharmaceutical composition in preparation of a drug for preventing and/or treating a disease caused by a HPV infection in combination with one or more of radiotherapy, chemotherapy, and therapeutic vaccine, wherein the disease is a solid tumor and the solid tumor comprises, but is not limited to, cervical cancer, vulvar cancer, penile cancer, anal cancer, and oral cancer.

In order to investigate the mechanism of the inhibiting effect of the polypeptide, a high throughput and quantitative proteomic analysis were used to analyze changes in proteomes inside the cell and in the supernatant before and after the polypeptide was administrated. The separated protein was digested by trypsin, polypeptides produced from the digestion was labeled by iTRAQ 4-plex reagents, and the labeled polypeptides were quantitatively analyzed by using a system combining a nano high performance liquid chromatography and a triple time of flight mass spectrometer. The results showed that several key signaling pathways related to the cellular immunity were activated or inhibited. Taken FIG. 4 as an example, as compared to those untreated, TEC kinase signaling pathway was obviously activated by the F1 polypeptide and the F3 polypeptide, which leaded to the apoptosis of the tumor cell. Besides, the F3 polypeptide and a control polypeptide P3 were labeled by fluorescent dye fluorescein isothiocyanate (FITC), incubated together with TC-1 cells for different periods, and repeatedly washed, thereafter a fluorescence intensity of FITC in the TC-1 cell was detected by a flow cytometry (FIG. 5A).

In another experiment, the location of the F3 polypeptide labeled by FITC in the TC-1 cell was detected by a confocal microscopy (FIG. 5B), so that the interaction between the F1 or F3 polypeptide and TC-1 cell could be known. When the polypeptide F3 and TC-1 were incubated together, FITC was found in TC-1 cell at $15^{th}$ minute, the peak fluorescence intensity of FITC was achieved at $2^{nd}$ hour, subsequently the fluorescence intensity of FITC was gradually weakened and maintained at the level of $15^{th}$ minute. Besides, the confocal microscopy results showed that after the F3 polypeptide and TC-1 were incubated together for 1 hour, the F3 polypeptide was penetrated through the cytomembrane of the TC-1 cell and distributed non-uniformly in the cytoplasm. The F1 and F3 polypeptides may act on the cytomembrane since they greatly change the cell migration, attachment, and actin cytoskeleton remodeling.

The two kinds of pharmaceutical compositions provided in the present disclosure have advantages of unique drug function mechanism, short course of treatment in use, less dosage of active component, obvious curative effect, low recurrent rate, slight side effect, and low treatment cost, which provides the patients with a great treating approach.

BRIEF DESCRIPTION OF THE DRAWINGS

FIG. 5 is a graph illustrating an interaction between the F3 polypeptide and the TC-1 cell according to an embodiment of the present disclosure.

FIG. 6 is a graph illustrating inhibiting effects of the F1 polypeptide, the F3 polypeptide, and Imiquimod administered separately and in combination on growth of TC-1 tumor cells in vitro according to an embodiment of the present disclosure.

FIG. 15A to FIG. 15B are graphs illustrating infiltrations of HPV16E7 specific CD8+T cells into spleen and tissues of tumors after injecting PBS, a mixture of the F1 polypeptide and the F3 polypeptide, the immune vaccine, and a mixture of the F1 polypeptide, the F3 polypeptide, and the immune vaccine into tumor-bearing mice.

FIG. 16A to FIG. 16D are photos illustrating states of a thermosensitive gel prepared by the F1 polypeptide and/or the F3 polypeptide at different temperatures.

FIG. 21A to FIG. 21H are graphs illustrating weights and hematoxylin-eosin staining of tumors of nude mice treated with P3 polypeptide gel, Imiquimod, a gel having no active component, a gel containing the F1 polypeptide and the F3 polypeptide, the gel having no active component in combination with Imiquimod, and the gel containing the F1 polypeptide and the F3 polypeptide in combination with Imiquimod.

DETAILED DESCRIPTION

Figure 1A:
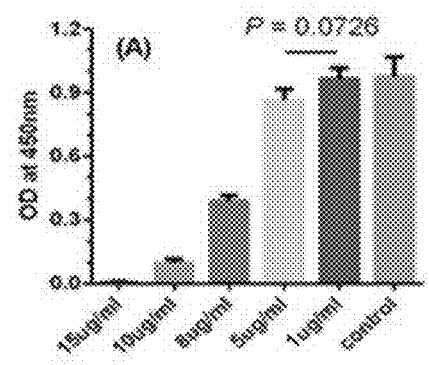
FIG. 1 is a graph illustrating inhibiting effects of the F1 polypeptide and the F3 polypeptide on growth of TC-1 tumor cells in vitro according to an embodiment of the present disclosure.
Figure 1B:
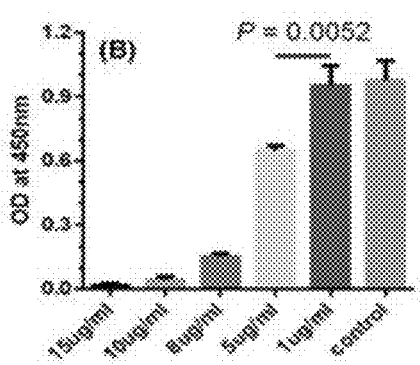
Figure 1C:
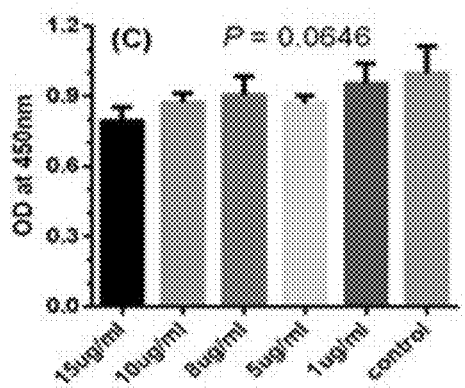
Figure 1D:
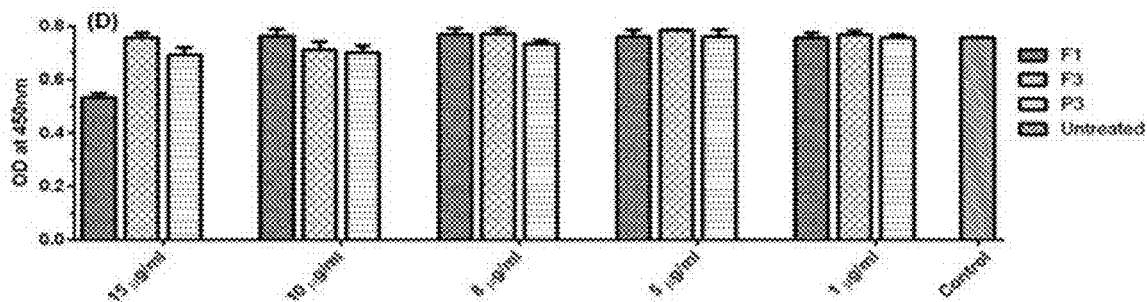
Figure 2:
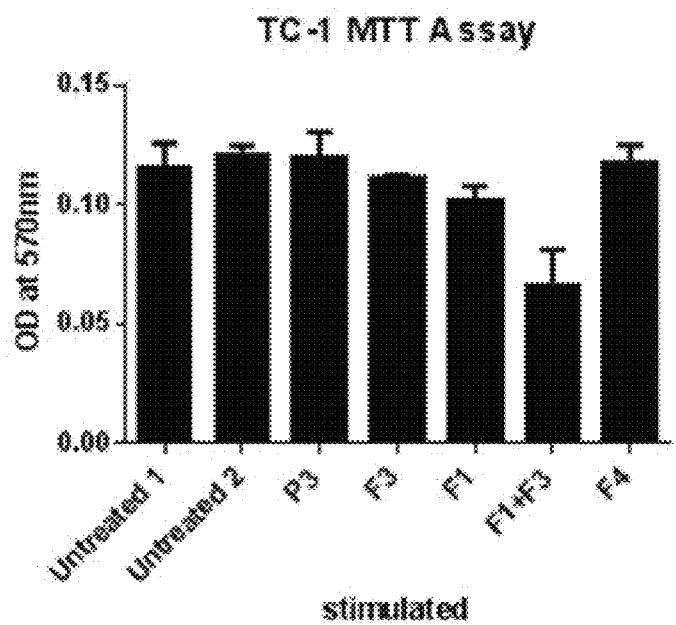
FIG. 2 is a graph illustrating a superimposed inhibiting effect of the F1 polypeptide in combination with the F3 polypeptide on growth of TC-1 tumor cells in vitro according to an embodiment of the present disclosure.
Figure 3:
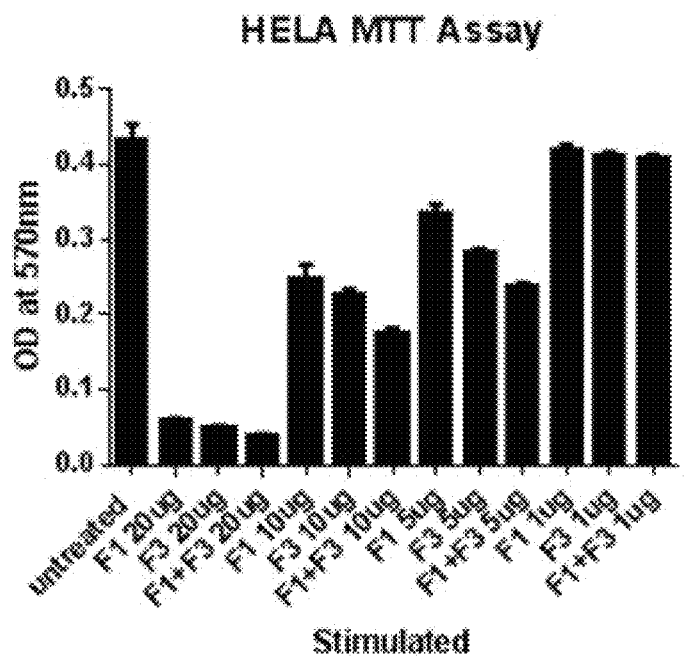
FIG. 3 is a graph illustrating a superimposed inhibiting effect of the F1 polypeptide in combination with the F3 polypeptide on growth of human cervical carcinoma cells (HELA) in vitro according to an embodiment of the present disclosure.
Figure 4:
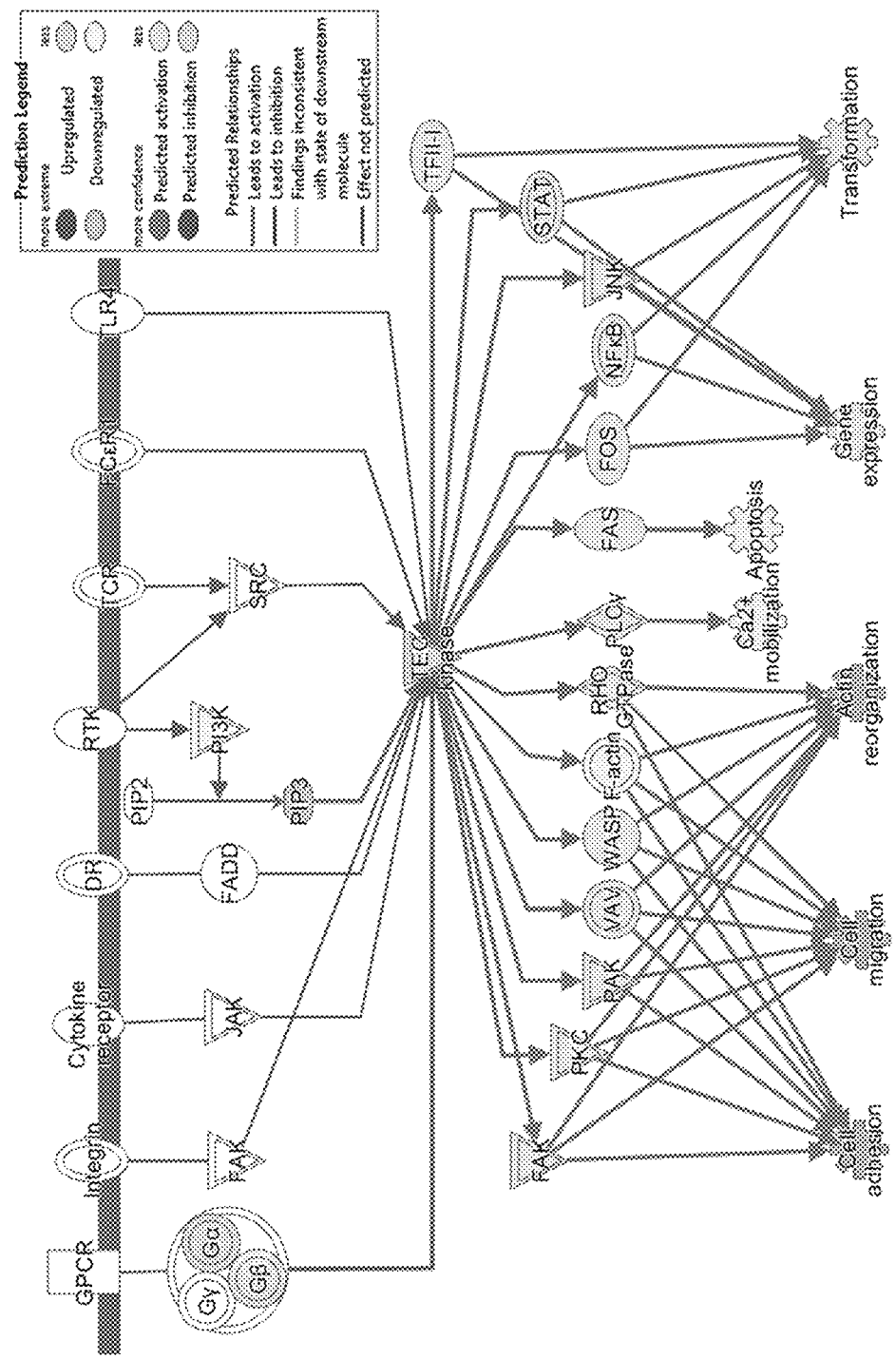
FIG. 4 is a graph illustrating a high throughput proteomic analysis for the F1 polypeptide and the F3 polypeptide according to an embodiment of the present disclosure.

Process parameters herein can be modified appropriately by those skilled in the art with reference to this specification. It should be noted that all similar replacements and modifications will be apparent to those skilled in the art and thus should be included in the present invention.

Types of instruments used in the present disclosure:

High throughput high performance liquid chromatography-mass spectrometry: Shimadzu Prominance nano reversed phase high performance liquid chromatography-ABSCIEX triple time of flight mass spectrometer configured with nano electrospray ion source.

EXAMPLE 1

Preparation of F1 Polypeptide and F3 Polypeptide 1) firstly a tree frog was induced to secrete a thick liquid with a white appearance by stimulating with a direct current having a voltage of 9 volt, wherein the tree frog was from a coastal rainforest of eastern Australia;

2) the liquid was collected and transferred into a solution containing 20 wt % methanol in ultrapure water, and vibrated and then filtered by a PVDF membrane having a pore diameter of 0.45 µm;

3) a clear liquid was filtered out and dried in a low temperature vacuum centrifugal dryer to form a white solid powder;

4) the white solid powder was dissolved into a solution having 0.1 wt % trifluoroacetic acid, and a sequence of peptide therein and a post-translational modification possessed by the peptide were analyzed by a high throughput high performance liquid chromatography-mass spectrometry;

5) the F1 polypeptide or the F3 polypeptide was synthesized respectively by employing a solid phase peptide synthesis according the sequence of peptide and the post-translational modification analyzed, specifically comprising the steps of:

a) on a CS336X peptide synthesizer, with a chloromethyl polystyrene resin as an insoluble solid state carrier, a C-terminal amino acid of the F1 polypeptide or the F3 polypeptide (an amino acid with its amino protected by a blocking group) was covalently attached to the solid state carrier;

b) the protecting group of the amino was removed under an action of trifluoroacetic acid, so that a first amino acid was attached to the solid state carrier;

c) a carboxyl of a second amino acid having its amino blocked is activated by N,N'-dicyclohexylcarbodiimide, (DCC, dicyclohexylcarbodiimide), and the second amino acid having its carboxyl activated by DCC is reacted with the amino of the first amino acid attached to the solid state carrier to form a peptide bond, so that a dipeptide with a protecting group was produced on the solid state carrier;

d) the above peptide forming reaction was repeated to cause a peptide chain to grow from C-terminal to N-terminal until achieving a required chain length, finally the protecting group was removed, and a deprotection and depolymerization for the resin is performed spontaneously in a solution of TFA/DCM/H$_2$O/TIPS with a volume ratio of 90:5:2.5:2.5;

d) the F1 polypeptide or the F3 polypeptide was obtained by precipitating with 10 equivalents of cold either and purifying by a reversed phase high performance liquid chromatography.

Particularly, carboxyls on side chains of glutamic acid and serine were protected by t-Bu, and a side chain of histidine were protected by Boc group to prevent a racemization of the histidine.

EXAMPLE 2

Preparation of Ointment Composition (with an Amount of 10 g) Containing the F1 Polypeptide and the F3 Polypeptide Formula:
F1 polypeptide: 10 mg;
F3 polypeptide: 10 mg;
PEG4000: 100 mg;
arginine: 20 mg;
PEG400: appropriate amount, added to reach 10 g.

The ointment composition was prepared according to a conventional method and sub-packed into aluminum pipes for packing the ointment. Each pipe has 2 mg, 5 mg, or 10 mg of the ointment.

EXAMPLE 3

Preparation of Ointment Composition (with an Amount of 10 g) Containing F1 Polypeptide, F3 Polypeptide and Imiquimod Formula:
F1 polypeptide: 2.5 mg;
F3 polypeptide: 2.5 mg;
Imiquimod: 30 mg;
PEG3000: 100 mg;
lysine: 5 mg;
PEG200: appropriate amount, added to reach 10 g.

The ointment composition was prepared according to a conventional method and sub-packed into aluminum pipes for packing the ointment. Each pipe has 2 mg, 5 mg, or 10 mg of the ointment.

EXAMPLE 4

Preparation of Emulsifiable Paste Composition (with an Amount of 10 g) Containing F1 Polypeptide and F3 Polypeptide Preparation of Matrix:
20 g of stearic acid, 1 g of ethylparaben, 2 g of white vaseline, 16 g of liquid paraffin, 5 g of glycerinum, 1 g of triethanolamine, 8 g of octadecanol, 6 g of wool fat, and an appropriate amount of distilled water were taken and formulated as 100 g of a matrix for later use.

Formula:

F1 polypeptide: 10 mg;

F3 polypeptide: 10 mg;

matrix: appropriate amount, added to reach 10 g.

The emulsifiable paste composition was prepared according to a conventional method and sub-packed into aluminum pipes for packing the emulsifiable paste. Each pipe has 2 mg, 5 mg, or 10 mg of the emulsifiable paste.

EXAMPLE 5

Preparation of Emulsifiable Paste Composition (with an Amount of 10 g) Containing F1 Polypeptide, F3 Polypeptide and Imiquimod Formula:

F1 polypeptide: 5 mg;

F3 polypeptide: 5 mg;

Imiquimod: 60 mg;

matrix: appropriate amount, added to reach 10 g.

The emulsifiable paste composition was prepared according to a conventional method and sub-packed into aluminium pipes for packing the emulsifiable paste. Each pipe has 2 mg, 5 mg, or 10 mg of the emulsifiable paste.

Clinical Trial

1. Inhibiting effects of F1, F3, and F1+F3 on growth of HPV transformed cells (TC-1 cells) in vitro Referring to FIGS. 1A to 1D, the inhibiting effects of F1, F3, and F1+F3 on growth of HPV transformed cells (TC-1 cell) in vitro were studied.

More specifically, in the method, 100 μL of $5\times10^3$ TC-1 cells cultured in a RPMI medium containing 10% of calf serum were added into a 96-well cell culture plate, the F1 polypeptide (FIG. 1A), the F3 polypeptide (FIG. 1B), and control polypeptide P3 (FIG. 1C) with different concentrations were added respectively and incubated overnight in an incubator with 5% of $CO_2$ at 37° C., and the cell proliferation was determined by a MTT assay.

Immortalized normal cells NP69 were used in another experiment. More specifically, 100 μL of $5\times10^3$ NP69 cells cultured in a RPMI medium containing 10% of calf serum were added into a 96-well cell culture plate, the F1 polypeptide, the F3 polypeptide, and control polypeptide P3 (FIG. 1D) with different concentrations were added respectively and incubated overnight in an incubator with 5% of $CO_2$ at 37° C., and the cell proliferation was determined by a MTT assay.

The results showed that the F1 polypeptide and the F3 polypeptide had obvious inhibiting effects on growth of TC-1 cells and the P3 polypeptide had no inhibiting effect. The F1 polypeptide, the F3 polypeptide, and the P3 polypeptide all had no inhibiting effect on NP69 cells.

2. mouse TC-1 tumor cells transformed by HPV16E7 can be killed better by Imiquimod in combination with the F1 polypeptide and the F3 polypeptide FIG. 2 is a graph showing a superimposed inhibiting effect of the F1 polypeptide in combination with the F3 polypeptide on growth of TC-1 tumor cells in vitro.

100 μL of $5\times10^3$ TC-1 cells cultured in a RPMI medium containing 10% of calf serum were added into a 96-well cell culture plate, 5 μg/mL of F1 and/or F3 and control polypeptides P3 and F4 were added respectively and incubated overnight in an incubator with 5% of $CO_2$ at 37° C., and the cell proliferation was determined by a MTT assay.

The results showed that there was a synergistic inhibiting effect between the F1 polypeptide and the F3 polypeptide on growth of TC-1.

3. human cervical carcinoma cells (HELA) transformed by HPV18E7 can be killed better by Imiquimod in combination with the F1 polypeptide and the F3 polypeptide FIG. 3 is a graph showing a superimposed inhibiting effect of the F1 polypeptide in combination with the F3 polypeptide on growth of human cervical carcinoma cells (HELA).

100 μL of $5\times10^3$ Hela cells cultured in a RPMI medium containing 10% of calf serum were added into a 96-well cell culture plate, F1 and/or F3 and control polypeptide P3 with different concentrations were added respectively and incubated overnight in an incubator with 5% of $CO_2$ at 37° C., and the cell proliferation was determined by a MTT assay.

The results showed that there was a synergistic inhibiting effect between the F1 polypeptide and the F3 polypeptide on growth of Hela cells.

FIG. 4 shows a high throughput and quantitative proteomic analysis for the F1 polypeptide and the F3 polypeptide showing that the TEC kinase signaling pathway was activated by the superimposed effect.

1000 μL of $5\times10^5$ TC-1 cells cultured in a RPMI medium containing 10% of calf serum were added into a 24-well cell culture plate, 1 μg/mL of a mixture of F1 and F3 polypeptides (with a ratio of 1:1) was added and incubated for 24 hours. The cells were collected, the protein was extracted and labeled by iTRAQ, and then the protein content in the cells was quantitatively analyzed by using reversed phase high performance liquid chromatography-mass spectrometer, the change in expression of protein was obtained by comparing with the cells cultured with no polypeptides F1 and F3, so as to analyze the changes of several signaling pathways in cells.

FIG. 5A and FIG. 5B are graphs showing an interaction between the F3 polypeptide and TC-1 cell.

1000 μL of $5\times10^5$ TC-1 cells cultured in a RPMI medium containing 10% of calf serum were added into a 24-well cell culture plate, 2 μg/mL of the F3 polypeptide labeled by FITC was added into the cells being incubated, cells at different time points of the incubation were collected and washed with PBS buffer solution, and then the relationship between the F3 polypeptide and TC-1 cell was observed by a flow cytometer (FIG. 5A) or a confocal microscopy (FIG. 5B).

It was shown that the F3 polypeptide can be combined with the TC-1 cell, peak was achieved at $2^{nd}$ hour, and the F3 polypeptide was distributed non-uniformly in the cytomembrane and the cytoplasm.

FIG. 6 is a graph showing inhibiting effects of the F1 polypeptide, the F3 polypeptide, and Imiquimod administered separately and in combination on growth of TC-1 tumor cells in vitro.

100 μL of $5\times10^3$ TC-1 cells cultured in a RPMI medium containing 10% of calf serum were added into a 96-well cell culture plate, 5 μg/mL of F1 and/or F3 and/or Imiquimod were added respectively and incubated overnight in an incubator with 5% of $CO_2$ at 37° C., and the cell proliferation was determined by a MTT assay.

The results showed that there were superimposed inhibiting effects between Imiquimod and F1 and/or F3 on growth of TC-1 cell.

Inhibiting effects of the F1 polypeptide, the F3 polypeptide, and Imiquimod administered separately and in combination on growth of Hela tumor cells in vitro:

100 μL of $5\times10^3$ Hela cells cultured in a RPMI medium containing 10% of calf serum were added into a 96-well cell culture plate, F1 and/or F3 and/or Imiquimod with different concentrations were added respectively and incubated overnight in an incubator with 5% of $CO_2$ at 37° C., and the cell proliferation was determined by a MTT assay.

Figure 7:
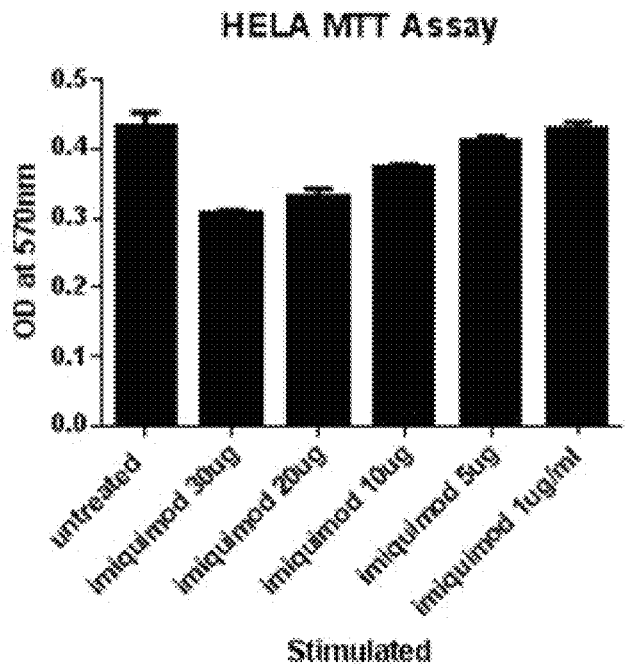
FIG. 7 is a graph illustrating inhibiting effects of different dosages of Imiquimod on growth of human cervical carcinoma cells (HELA) in vitro.

The results showed that Imiquimod had an inhibiting effect on growth of Hela cells in vitro, as shown in FIG. 7.

Figure 8:
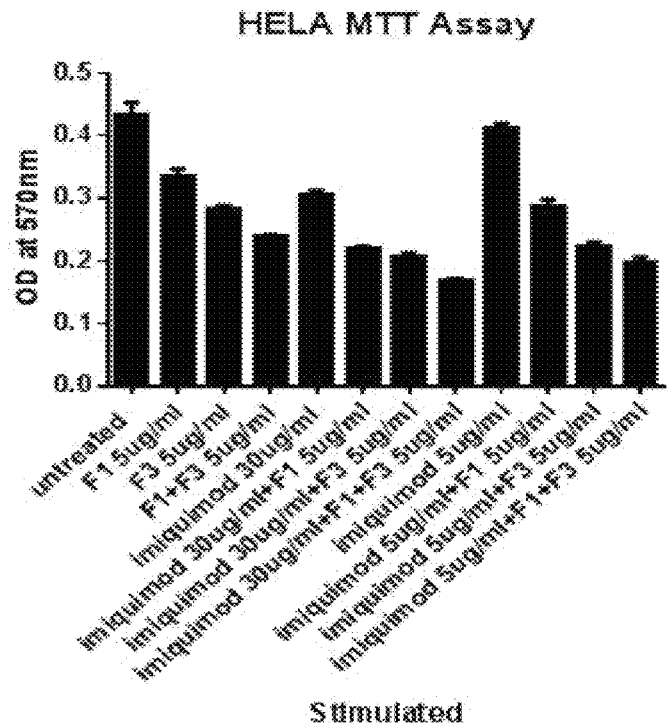
FIG. 8 is a graph illustrating inhibiting effects of the F1 polypeptide, the F3 polypeptide, and Imiquimod administered separately and in combination on growth of human cervical carcinoma cells (HELA) in vitro.

There were superimposed inhibiting effects between Imiquimod and F1 and/or F3 on growth of Hela cell in vitro, as shown in FIG. 8.

Western Blot Analysis

Figure 9A:
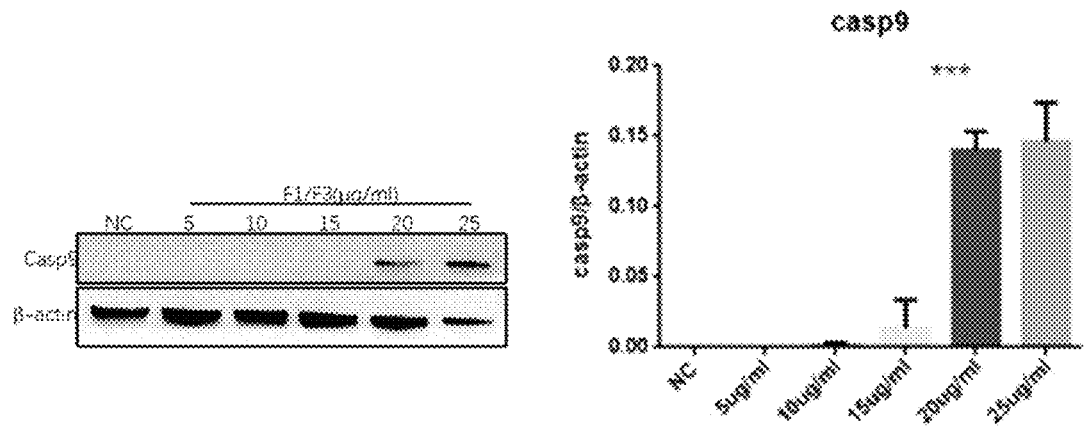
FIG. 9A to FIG. 9D are graphs illustrating expressions of CASP3, CASP9, p-AKT, and PI3K in Hela cells treated by a mixture of the F1 polypeptide and the F3 polypeptide (with a ratio of 1:1) in different concentrations.
Figure 9B:
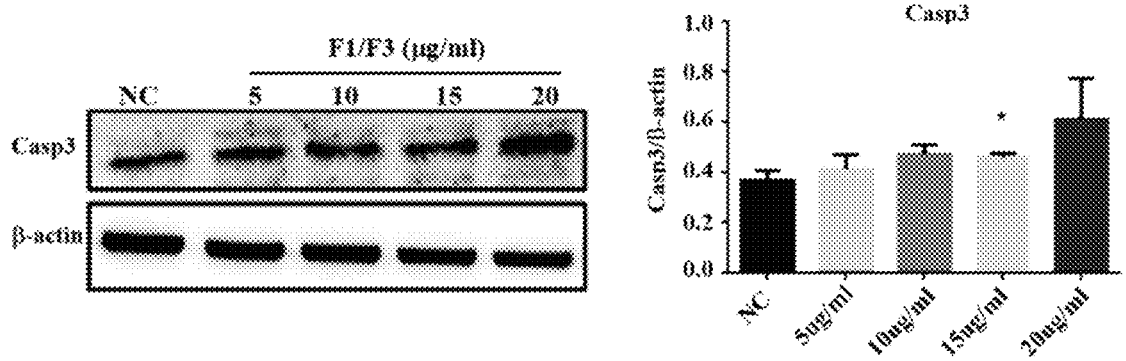
Figure 9C:
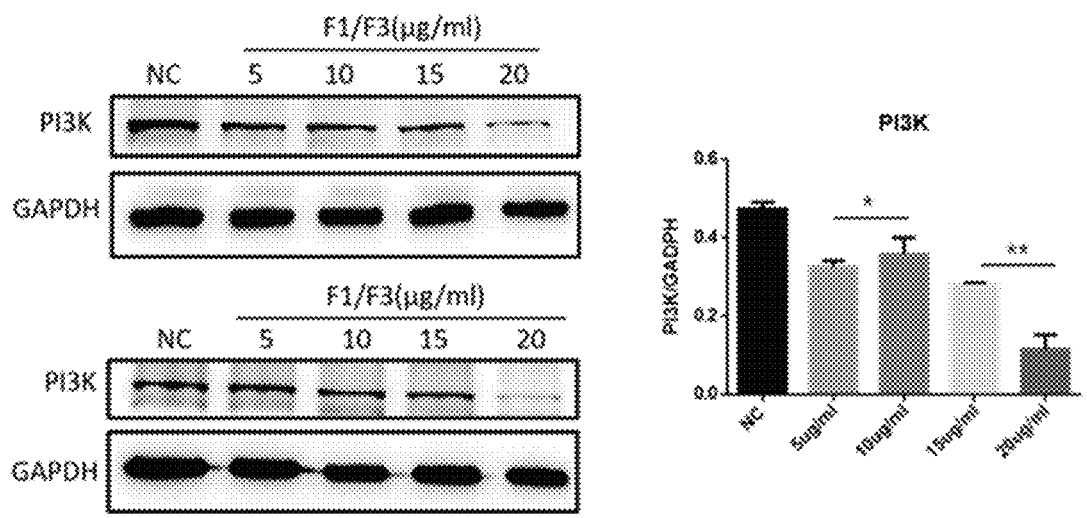
Figure 9D:
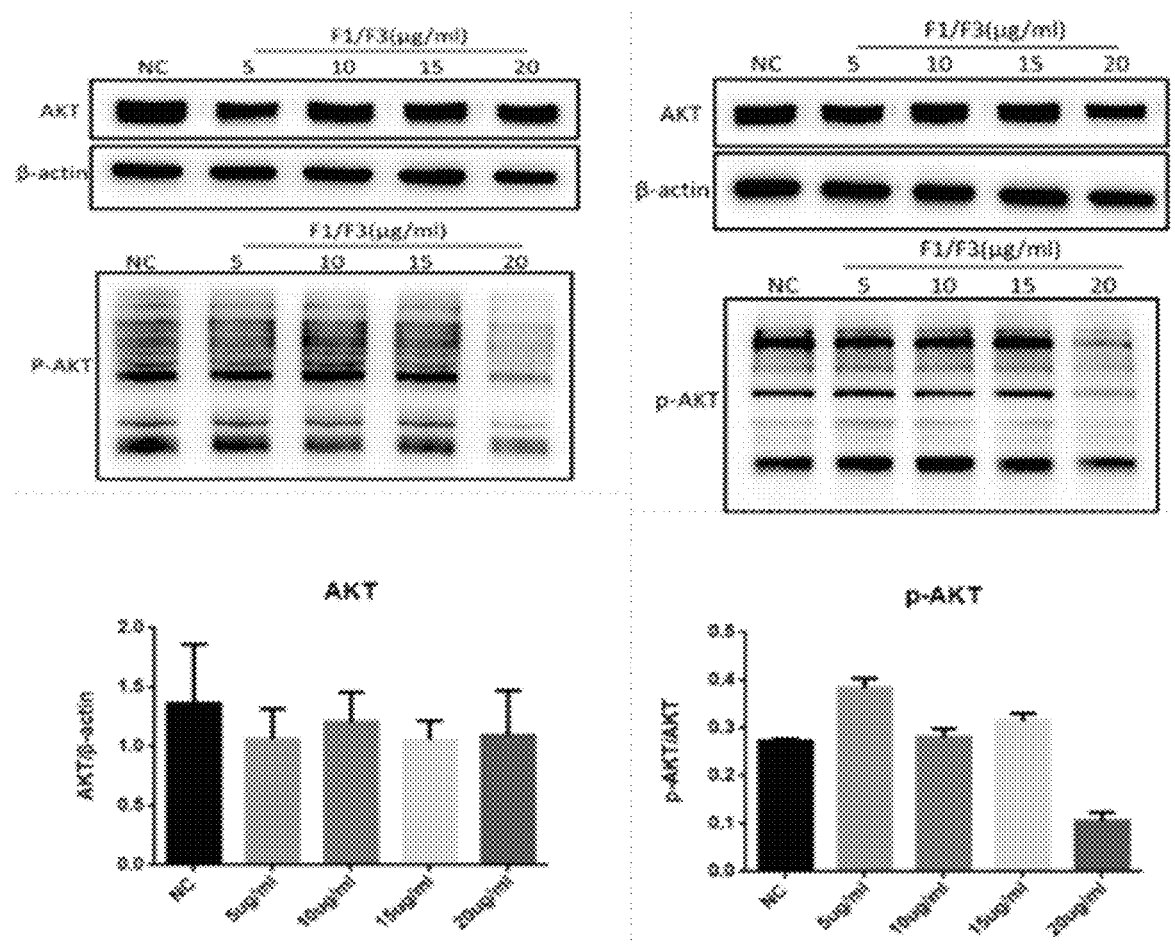

A mixture of the F1 polypeptide and the F3 polypeptide in a ratio of 1:1 was provided; $5\times10^5$ Hela cells were treated with the mixture in different concentrations for 24 hours respectively; and expressions of CASP3, CASP9, p-AKT, and PI3K are analyzed by Western Blot. Referring to FIG. 9A, it can be seen that expression levels of CASP3 and CASP9 (which induce apoptosis) in Hela cells treated by the mixture were higher than in Hela cells untreated by the mixture, and the increases were related positively to the concentrations of the mixture. Referring to 9B and 9C, it can be seen that expressions of p-AKT and PI3K in Hela cells were significantly inhibited by the mixture in a concentration of 20 μg/mL, suggesting that the PI3K-AKT signal transduction pathway may be one of important pathways through which the F1 polypeptide and/or F3 polypeptide influence the cell functions.

Stability in Vitro

Test 1

Figure 10A:
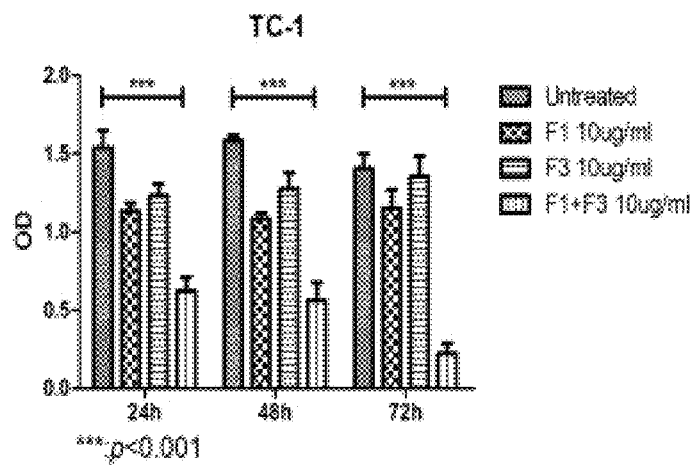
FIG. 10A is a graph illustrating inhibiting effects of the F1 polypeptide, the F3 polypeptide, and a mixture thereof on growth of TC-1 tumor cells in vitro at $24^{th}$ hour, $48^{th}$ hour, and $72^{th}$ hour respectively.

RPMI medium containing 10% of calf serum and $5\times10^3$ TC-1 cells were added into a 96-well cell culture plate; 10 μg/ml of the F1 polypeptide, the F3 polypeptide, and a mixture of F1 and F3 in a ratio of 1:1 were added respectively into the medium and incubated for 72 hours in an incubator with 5% of $CO_2$ at 37° C., and the cell proliferations at $24^{th}$ hour, $48^{th}$ hour, and $72^{th}$ hour were determined respectively by the MTT assay. Referring to FIG. 10A, it can be seen that the F1 polypeptide and/or F3 polypeptide exhibited significant inhibiting effects on growth of TC-1 cells even at $72^{th}$ hour.

Test 2

Figure 10B:
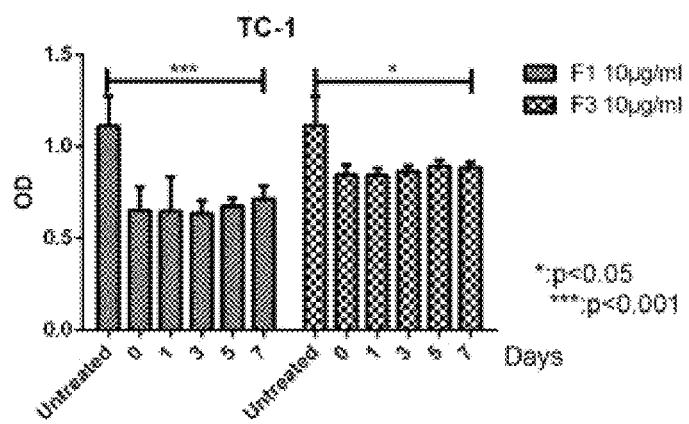
FIG. 10B is a graph showing inhibiting effects of the F1 polypeptide and the F3 polypeptide, which had been prepared and stored at room temperature for 1, 3, 5, and 7 days before using, on growth of TC-1 tumor cells in vitro.

The steps in the Test 2 were substantially the same as those in the Test 1, except that the F1 polypeptide and the F3 polypeptide which had been prepared and stored for 0, 1, 3, 5, and 7 days at minus 20° C. respectively before using were added into the medium, and the incubation was performed for 24 hours. Referring to FIG. 10B, it can be seen that the activities of the F1 polypeptide and the F3 polypeptide were not reduced even after being prepared and stored for 7 days, suggesting that the F1 polypeptide and the F3 polypeptide have high stabilities.

Test 3

Figure 10C:
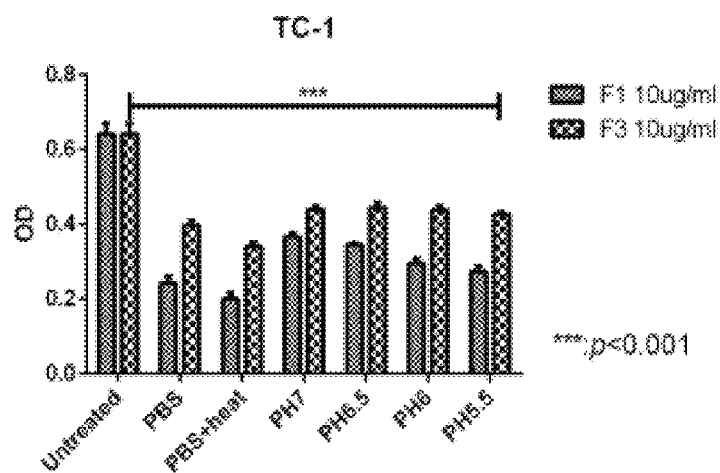
FIG. 10C is a graph showing inhibiting effects of the F1 polypeptide and the F3 polypeptide diluted by phosphate buffer saline which has different pH values or had been heated before dilatation.

The steps in the Test 3 were substantially the same as those in the Test 1, except that the pH value of the phosphate buffer saline (PBS) in the medium was changed or the PBS is heated for 10 minutes at 100° C. before using, and the incubation was performed for 24 hours. Referring to FIG. 10C, it can be seen that the F1 polypeptide and the F3 polypeptide were still active even in the PBS with a pH value of 5.5 or heated at 100° C.

Proteomic Analysis

Changes in signal transduction induced by TC-1 cells treated by a mixture of the F1 polypeptide and the F3 polypeptide were analyzed by a bioinformatics method. The results showed that totally 16 pathways were activated or inhibited, including several important pathways associated with immunity, such as PI3K-AKT, signaling pathways of Tec family kinases, and LXR/RXR pathway, indicating that a variety of cytokines, such as IL-6, IL-1β, MCP-1, and MCP-3, may be secreted by TC-1 cells treated by the F1 and/or F3 (the secretion of IL-6 has been demonstrated by FIGS. 12A and 12B). Referring to FIG. 11C, it can be seen that NF-κB on the LXR/RXR pathway were significantly increased, thereby activating downstream iNOS, COX-2, IL-6/1β, MCP-1/3, and MMP9, which are important inflammatory mediators. LXR, RXR, and NCOR were significantly inhibited, suggesting that downstream control factors, including LPL, ABCA-1, ABCG-1/4, SREBP-1c, APO-C1/2/4, UGT1A3, and Arg-2, were activated. Consequently, cellular cholesterol transport and efflux and lipid synthesis were inhibited and inflammatory response was enhanced.

Figure 11A:
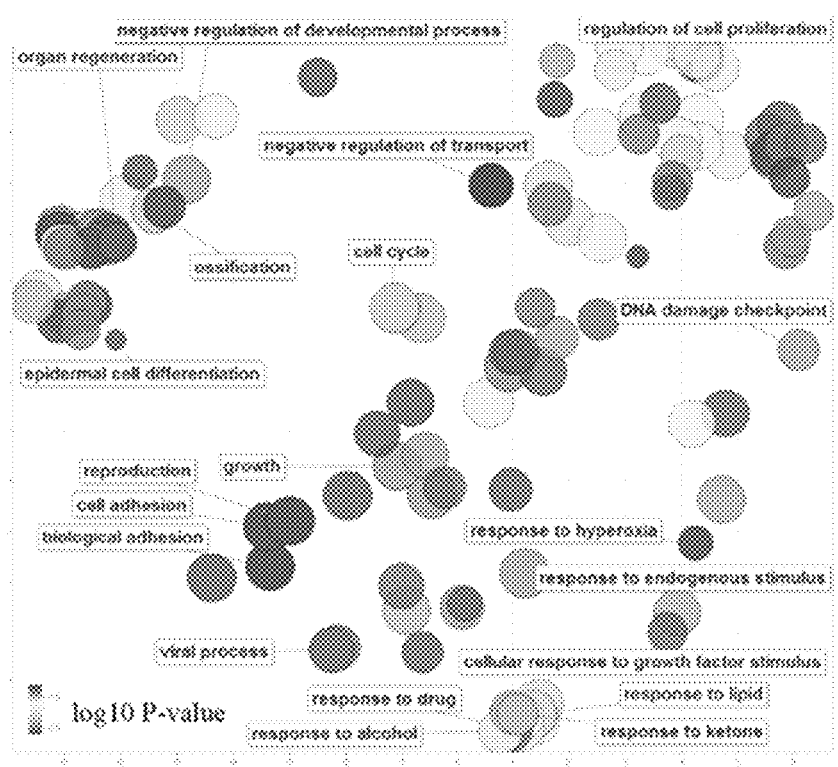
FIG. 11A is a graph illustrating proteins having significant changes in expression due to a F1 and/or F3 polypeptide treatment and gene functions of the proteins.
Figure 11B:
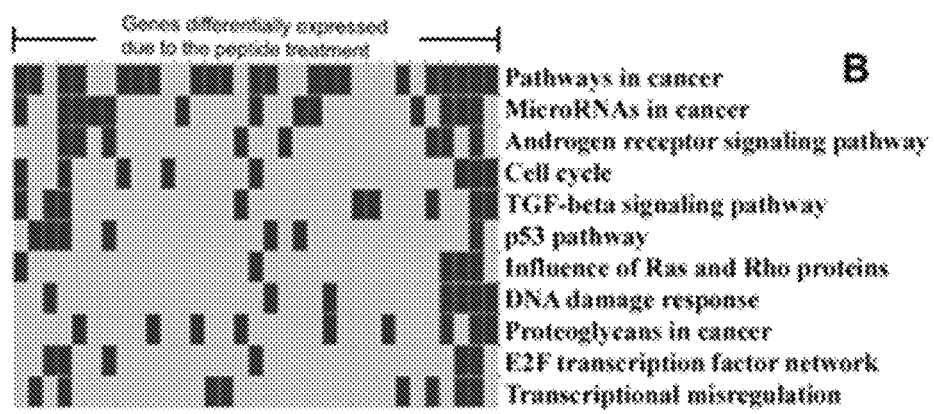
FIG. 11B is a graph illustrating KEGG pathways on which proteins having significant changes in expression due to a F1 and/or F3 polypeptide treatment are concentrated.
Figure 11C:
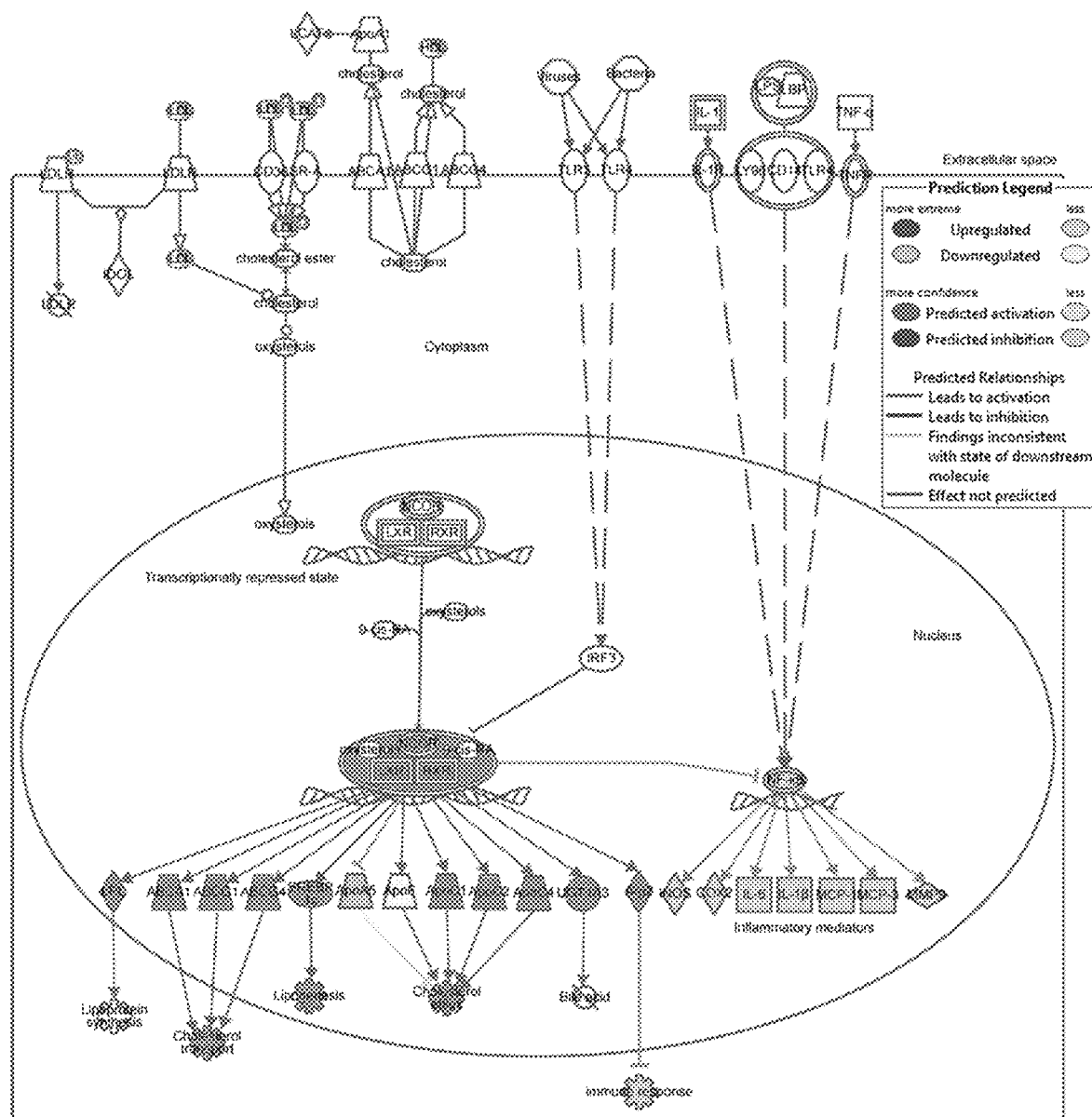
FIG. 11C is a graph illustrating an iTRAQ quantitative analysis for proteins secreted by TC-1 cells.

Referring to FIG. 11A, it can be seen that the cell proliferation was significantly inhibited, the expression levels of some genes associated with the growth, attachment, and regeneration of cells were increased, suggesting that these functions may have been damaged by the F1 and/or F3. Referring to FIG. 11B, it can be seen that a majority of genes, associated with pathways related to cancer, are differentially expressed due to the F1 and/or F3 treatment. For example, microRNA, p53, or DNA in cancer cells were damaged or mis-controlled.

Figure 12A:
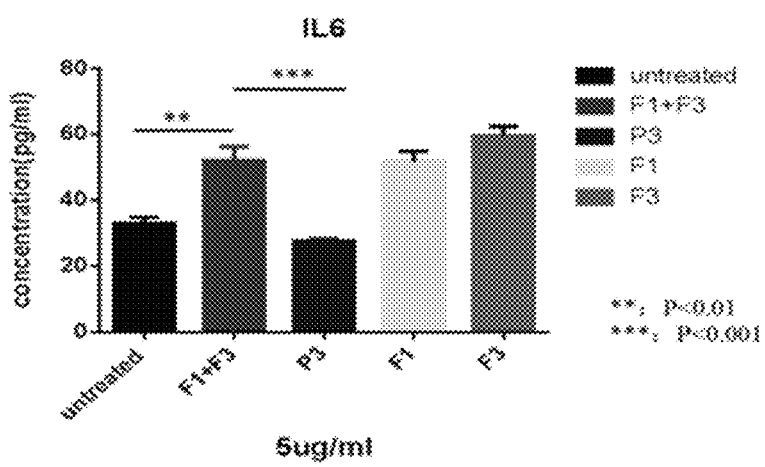
FIG. 12A is a graph illustrating IL-6 levels (detected by ELISA) in TC-1 culture solutions treated by 5 μg/mL of P3 polypeptide, the F1 polypeptide, the F3 polypeptide, and the F1 and F3 polypeptides overnight, respectively.
Figure 12B:
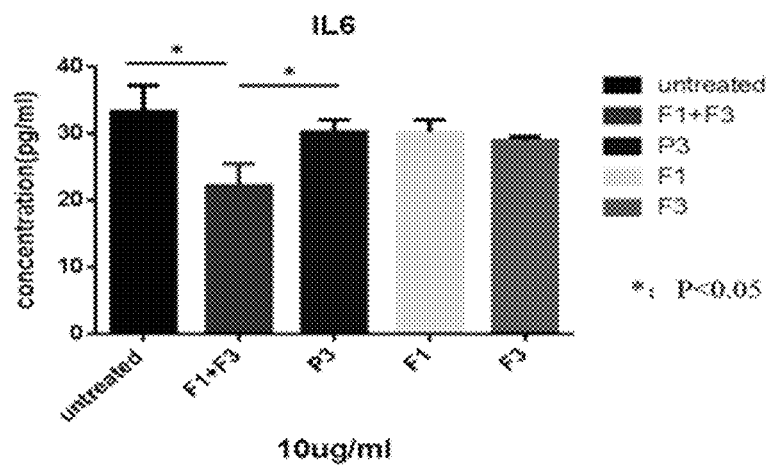
FIG. 12B is a graph illustrating IL-6 levels (detected by ELISA) in TC-1 culture solutions treated by 10 μm/mL of P3 polypeptide, the F1 polypeptide, the F3 polypeptide, and the F1 and F3 polypeptides overnight, respectively.

FIGS. 12A and 12B are graphs illustrating IL-6 levels (detected by ELISA) in TC-1 culture solutions treated by 5 μg/mL and 10 μg/mL of the P3 polypeptide, the F1 polypeptide, the F3 polypeptide, and a mixture of F1 and F3 overnight, respectively. It can be seen that the IL-6 level in TC-1 culture solution treated by 5 μg/mL of the F1 polypeptide, the F3 polypeptide, or the mixture of F1 and F3 was significantly higher than that untreated solution or solution treated by the P3 polypeptide. IL-6 levels were decreased with increase of concentration of the F1 polypeptide, the F3 polypeptide, or the mixture of F1 and F3, which may be resulted from apoptosis of TC-1 cells induced by high concentration of the F1 polypeptide, the F3 polypeptide, or the mixture of F1 and F3.

Inhibiting Effect on TC-1 Cell

Test 4

Figure 13A:
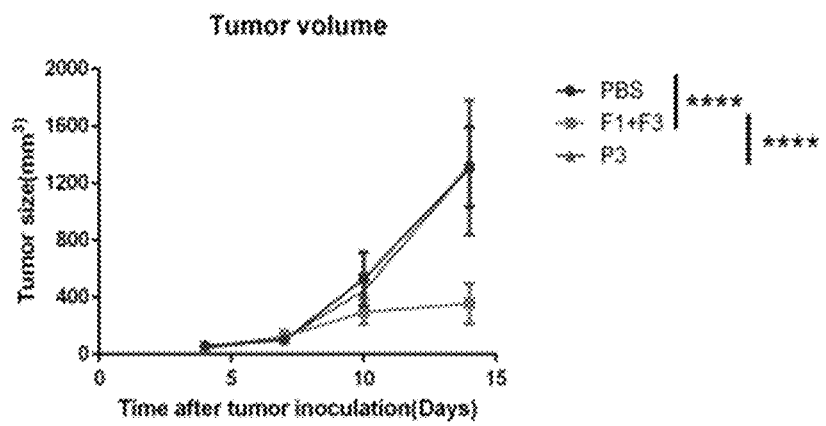
FIG. 13A is a graph illustrating tumor sizes over time in C57BL/6 mice inoculated with TC-1 cells subcutaneously and injected with PBS, a mixture of F1 and F3 polypeptides, and P3 polypeptide.
Figure 13B:
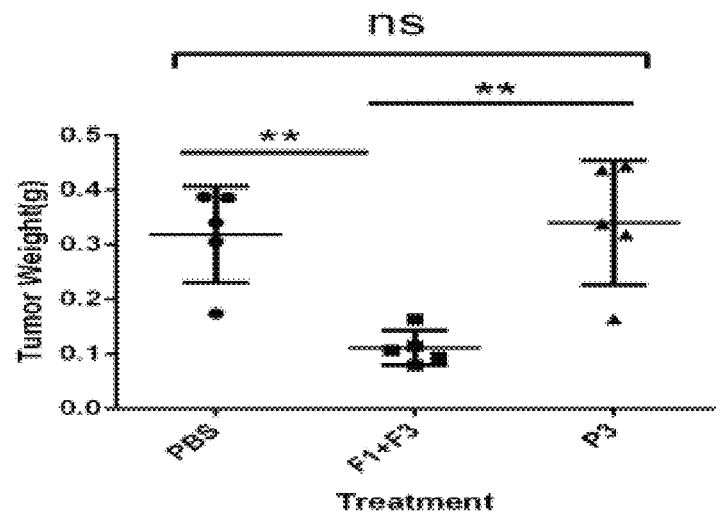
FIG. 13B is a graph illustrating tumor weights in C57BL/6 mice inoculated with TC-1 cells subcutaneously and injected with PBS, a mixture of F1 and F3 polypeptides, and P3 polypeptide.

C57BL/6 mice were respectively inoculated with $5 \times 10^5$ TC-1 cells subcutaneously. After 5 days of inoculation, tumors had grown and PBS, a mixture of the F1 polypeptide and the F3 polypeptide, and the P3 polypeptide were injected into the tumors respectively and consecutively for five days, after another five days, the tumors are isolated and weighted. The sizes of the tumors observed were shown in FIG. 13A and the weights of the tumors were shown in FIG. 13B. It can be seen that both the sizes and the weights of tumors of mice injected with the mixture of the F1 polypeptide and the F3 polypeptide were smaller those of mice injected with PBS or P3 polypeptide, suggesting that the mixture of the F1 polypeptide and the F3 polypeptide had higher inhibiting effect on the tumor as compared to PBS and P3 polypeptide.

Test 5

Figure 13C:
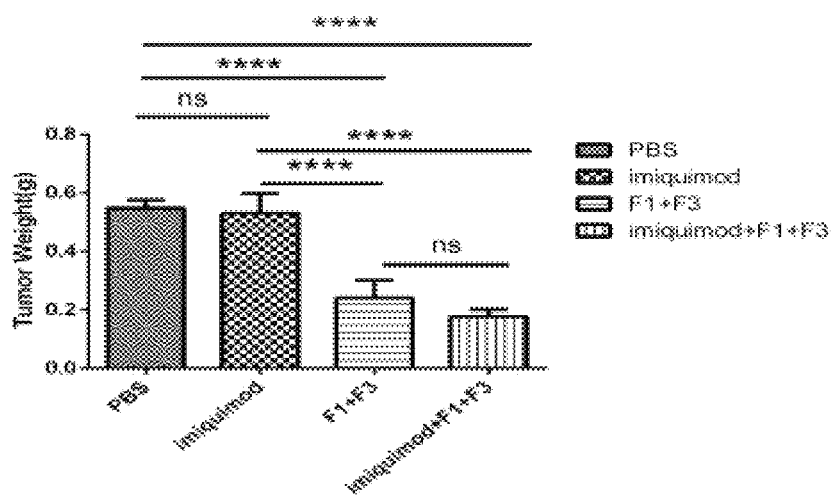
FIG. 13C is a graph illustrating tumor weights in C57BL/6 mice inoculated with TC-1 cells subcutaneously and injected with PBS, Imiquimod, a mixture of F1 and F3 polypeptides, and a mixture of F1 polypeptide, F3 polypeptide, and Imiquimod.
Figure 13D:
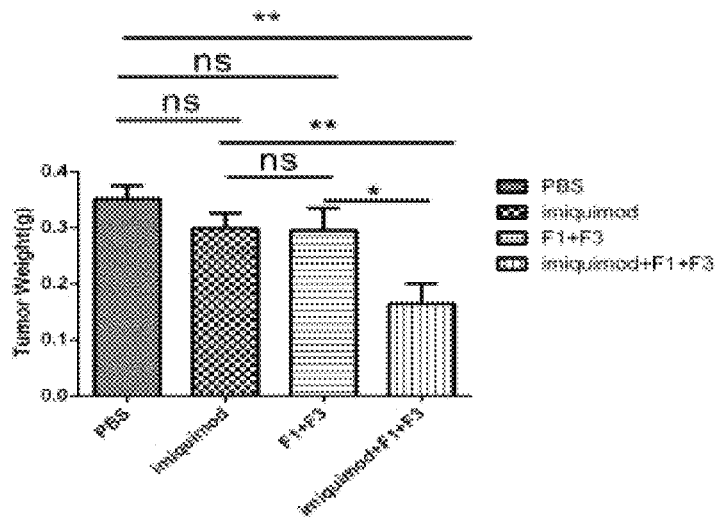
FIG. 13D is a graph illustrating tumor weights in nude mice inoculated with TC-1 cells subcutaneously and injected with PBS, Imiquimod, a mixture of F1 and F3 polypeptides, and a mixture of F1 polypeptide, F3 polypeptide, and Imiquimod.

The steps in the Test 5 were substantially the same as those in the Test 4, except that both the C57BL/6 mice and the nude mice were subjected to the test, and PBS, Imiquimod, a mixture of F1 and F3 polypeptides, and a mixture of F1 polypeptide, F3 polypeptide, and Imiquimod were injected into the tumors. The results were shown in FIGS. 13C and 13D. It can be seen that the mixture of F1 and F3 polypeptides substantially had no inhibiting effect on tumor growths in nude mice (which has no specific immune cell), suggesting that the inhibiting effect on growth of TC-1 cells may caused by a specific immune response resulted from an apoptosis of TC-1 cell induced by the F1 polypeptide and/or the F3 polypeptide.

It is noteworthy that the amounts of LPS in all of polypeptides had been measured and the values measured were between 0.03 EU/ml and 0.44 EU/ml, so the influence of LPS to the test 4 and test 5 can be neglected.

Test 6

The steps in the Test 6 were substantially the same as those in the Test 4, except that the C57BL/6 mice were replaced by the tumor-bearing mice, and the tumors were injected with PBS, a mixture of F1 and F3 polypeptides, and/or a vaccine containing HPV16E7 polypeptide, MPLA, and α-Interleukin(IR)-10R (EX/MPLA/α-IR-10R vaccine). The survival rates of C57BL/6 mice were shown in FIG. 13E.

Test 7

The steps in the Test 7 were substantially the same as those in the Test 4, except that the C57BL/6 mice were replaced by the tumor-bearing mice, and the tumors were injected with PBS, a mixture of the F1 polypeptide, the F3 polypeptide, and the EX/MPLA/α-IR-10R vaccine, and a mixture of the F1 polypeptide, the F3 polypeptide, and a vaccine containing HPV16E7 polypeptide and MPLA (EX/MPLA vaccine). The survival rates of C57BL/6 mice were shown in FIG. 13F.

Figure 13E:
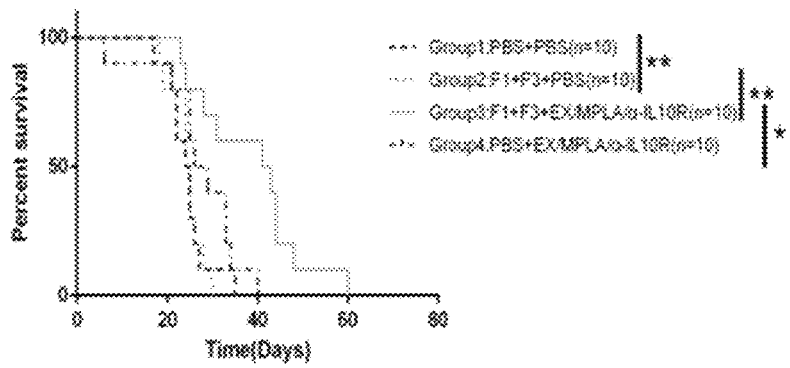
FIG. 13E is a graph illustrating survival rates of C57BL/6 mice inoculated with TC-1 cells subcutaneously and injected with PBS, a mixture of the F1 polypeptide and the F3 polypeptide, and/or a vaccine containing HPV16E7 polypeptide, MPLA, and α-Interleukin(IR)-10R (EX/MPLA/α-IR-10R vaccine)
Figure 13F:
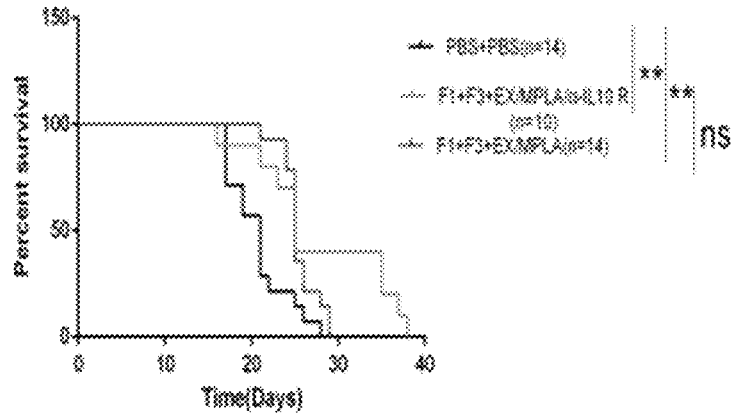
FIG. 13F is a graph illustrating survival rates of C57BL/6 mice inoculated with TC-1 cells subcutaneously and injected with PBS, a mixture of the F1 polypeptide, the F3 polypeptide, and the EX/MPLA/α-IR-10R vaccine, and a mixture of the F1 polypeptide, the F3 polypeptide, and a vaccine containing HPV16E7 polypeptide and MPLA, (EX/MPLA vaccine).
Figure 14A:
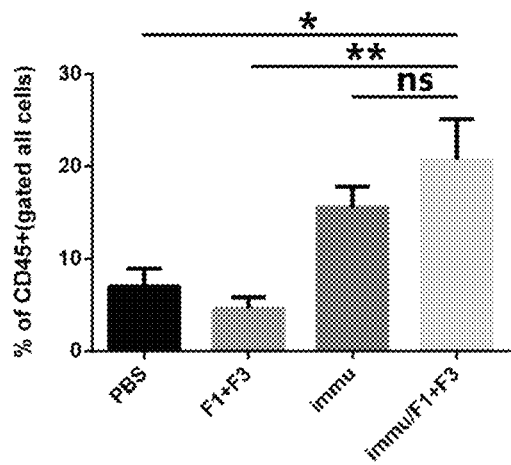
FIG. 14A to FIG. 14D are graphs illustrating infiltrations of immune cells into tissues of tumors after injecting PBS, a mixture of the F1 polypeptide and the F3 polypeptide, a immune vaccine (EX/MPLA/α-IR-10R vaccine), and a mixture of the F1 polypeptide, the F3 polypeptide, and the immune vaccine into tumor-bearing mice.
Figure 14B:
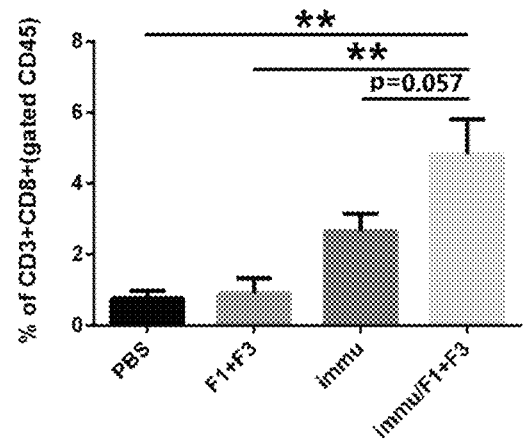
Figure 14C:
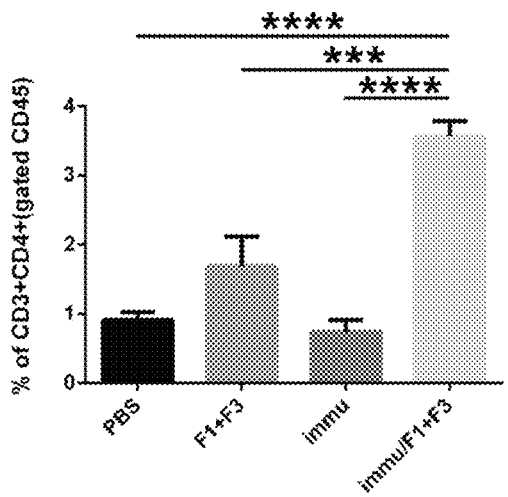
Figure 14D:
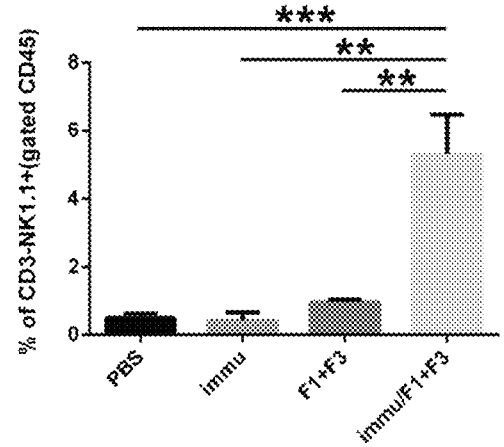
Figure 17A:
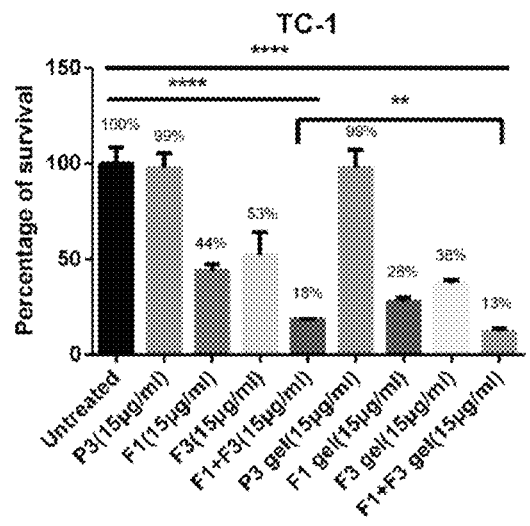
FIG. 17A to FIG. 17D are graphs illustrating survival rates of TC-1 cells and Hela cells treated by P3 polypeptide, F1 polypeptide, F3 polypeptide, a mixture of F1 and F3, and gels thereof with different concentrations in a MTT assay.
Figure 17B:
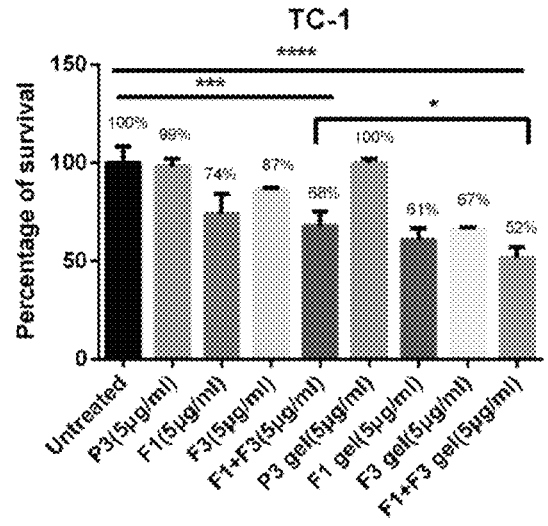
Figure 17C:
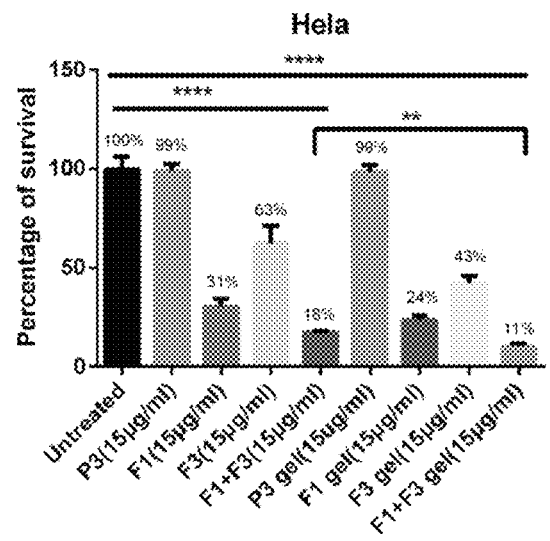
Figure 17D:
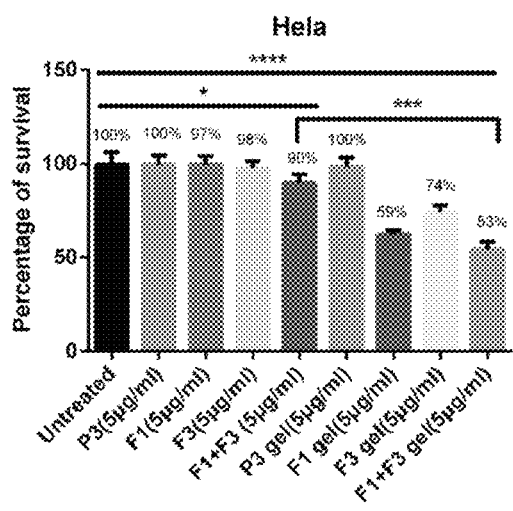
Figure 18A:
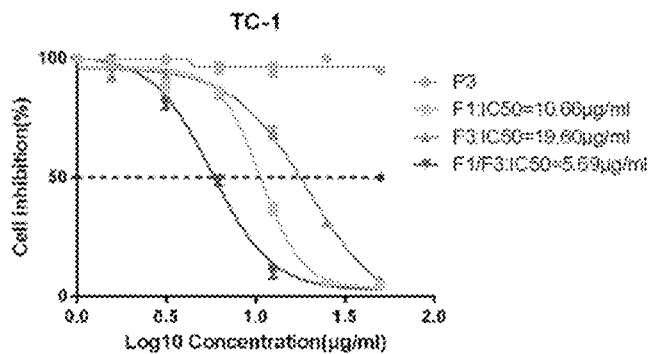
FIG. 18A to FIG. 18D are graphs illustrating IC50 values of P3 polypeptide, the F1 polypeptide, the F3 polypeptide, a mixture of F1 and F3, and gels thereof for TC-1 cells and Hela cells in the MTT assay.
Figure 18B:
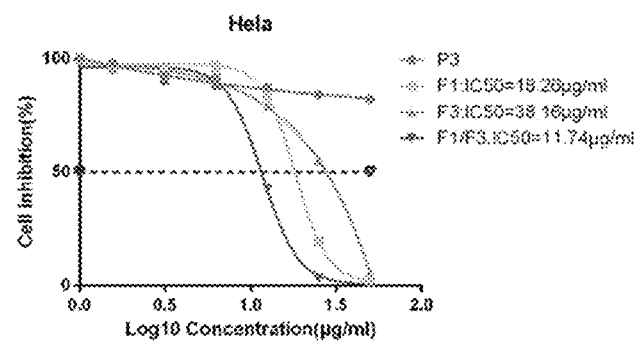
Figure 18C:
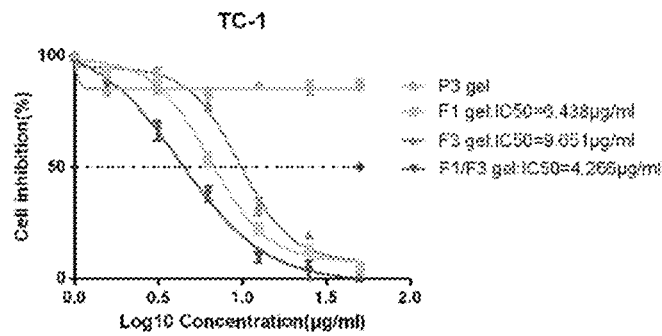
Figure 18D:
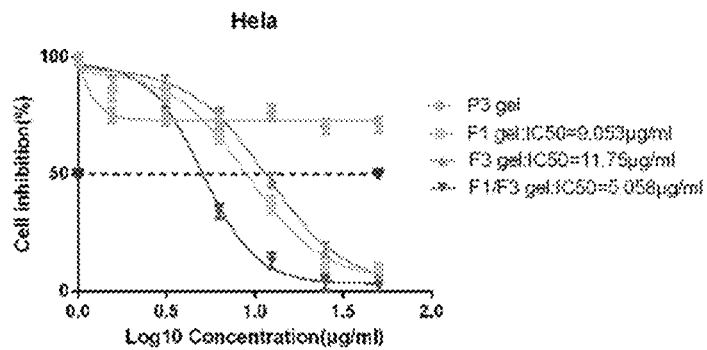

As shown in FIGS. 13E and 13F, the tumor-bearing mice injected only with the mixture of the F1 polypeptide and the F3 polypeptide or the vaccine have higher survival rate than the tumor-bearing mice injected with only the PBS. The tumor-bearing mice injected with both the mixture of the F1 polypeptide and the F3 polypeptide and the vaccine have significantly higher survival rate than the tumor-bearing mice injected with only the mixture of the F1 polypeptide and the F3 polypeptide or the vaccine. The tumor-bearing mice injected only with the EX/MPLA/α-IR-10R vaccine have higher survival rate than the tumor-bearing mice injected with only the PBS, and the tumor-bearing mice injected with the EX/MPLA/α-IR-10R vaccine have higher survival rate than the tumor-bearing mice injected with the EX/MPLA vaccine.

Infiltrations of Immune Cells into Tumor Tissue

FIGS. 14A to 14D are graphs illustrating infiltrations of immune cells into tissues of tumors after injecting PBS, a mixture of the F1 polypeptide and the F3 polypeptide, a immune vaccine (EX/MPLA/α-IR-10R vaccine), and a mixture of the F1 polypeptide, the F3 polypeptide, and the immune vaccine into tumor-bearing mice. It can be seen that more hematocytes including CD8+T cells, CD4+T cells, and NKT cells are attracted into the tissue of tumor treated by the mixture of the F1 polypeptide and the F3 polypeptide in combination with the vaccine as compared to that treated only by the mixture of the F1 polypeptide and the F3 polypeptide or the vaccine.

FIGS. 15A to 15B are graphs illustrating infiltrations of HPV16E7 specific CD8+T cells into spleen (FIG. 15A) and tissues of tumors (FIG. 15B) after injecting PBS, a mixture of the F1 polypeptide and the F3 polypeptide, the immune vaccine, and a mixture of the F1 polypeptide, the F3 polypeptide, and the immune vaccine into tumor-bearing mice. It can be seen that more HPV16E7 specific CD8+T cells are attacked into spleen and tissue of tumor treated by the mixture of the F1 polypeptide and the F3 polypeptide in combination with the vaccine as compared to that treated only by the mixture of the F1 polypeptide and the F3 polypeptide or the vaccine.

Thermosensitive Gel Prepared by the Caerin Polypeptide and Biological Activity Thereof Referring to FIGS. 16A to 16D, a thermosensitive gel is prepared by the F1 polypeptide and/or the F3 polypeptide. The thermosensitive gel is a colloidal solution at room temperature and 28-35° C. and is a gel at a physiological temperature.

FIGS. 17A to 17D are graphs illustrating survival rates TC-1 cells and Hela cells treated by P3 polypeptide, F1 polypeptide, F3 polypeptide, a mixture of F1 and F3, and gels thereof with different concentrations in a MTT assay. FIGS. 18A to 18D are graphs illustrating IC50 values of P3 polypeptide, the F1 polypeptide, the F3 polypeptide, a mixture of F1 and F3, and gels thereof for TC-1 cells and Hela cells in the MTT assay. It can be seen that the gels prepared by the F1 polypeptide and/or F3 polypeptide have similar inhibiting effects on growths of Hela cells and TC-1 cells in vitro as the F1 polypeptide and/or F3 polypeptide.

Figures 19A, 19B:
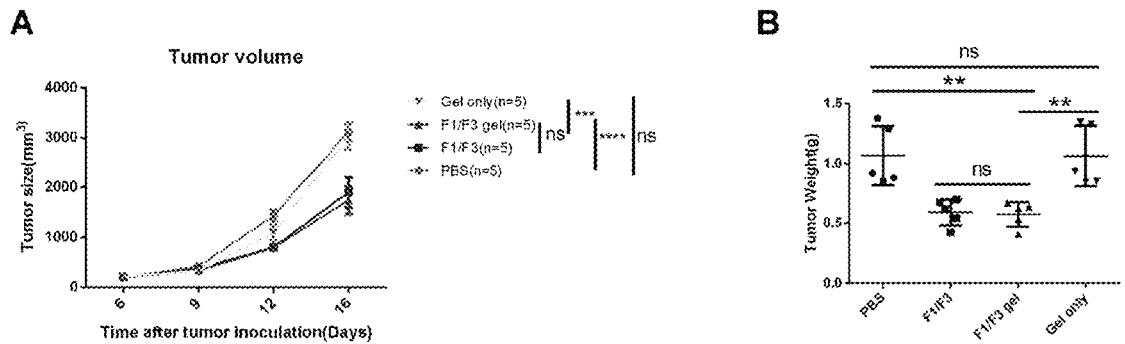
FIG. 19A is a graph illustrating tumor sizes in tumor-bearing mice inoculated with TC-1 cells subcutaneously and treated with the PBS, a mixture of F1 and F3, a gel having no active component, and a gel containing the F1 polypeptide and the F3 polypeptide.
FIG. 19B is a graph illustrating tumor weights in tumor-bearing mice inoculated with TC-1 cells subcutaneously and treated with the PBS, the mixture of F1 and F3, a gel having no active component, and the gel containing the F1 polypeptide and the F3 polypeptide.

FIG. 19A is a graph illustrating tumor sizes in tumor-bearing mice inoculated with TC-1 cells subcutaneously and treated with the PBS, a mixture of F1 and F3, a gel having no active component, and a gel containing the F1 polypeptide and the F3 polypeptide. FIG. 19B is a graph illustrating tumor weights in tumor-bearing mice inoculated with TC-1 cells subcutaneously and treated with the PBS, the mixture of F1 and F3, a gel having no active component, and the gel containing the F1 polypeptide and the F3 polypeptide. It can be seen that the gel containing the F1 polypeptide and the F3 polypeptide has a similar inhibiting effects on growth of TC-1 cells in vivo as the F1 polypeptide and the F3 polypeptide.

Figures 20A, 20B:
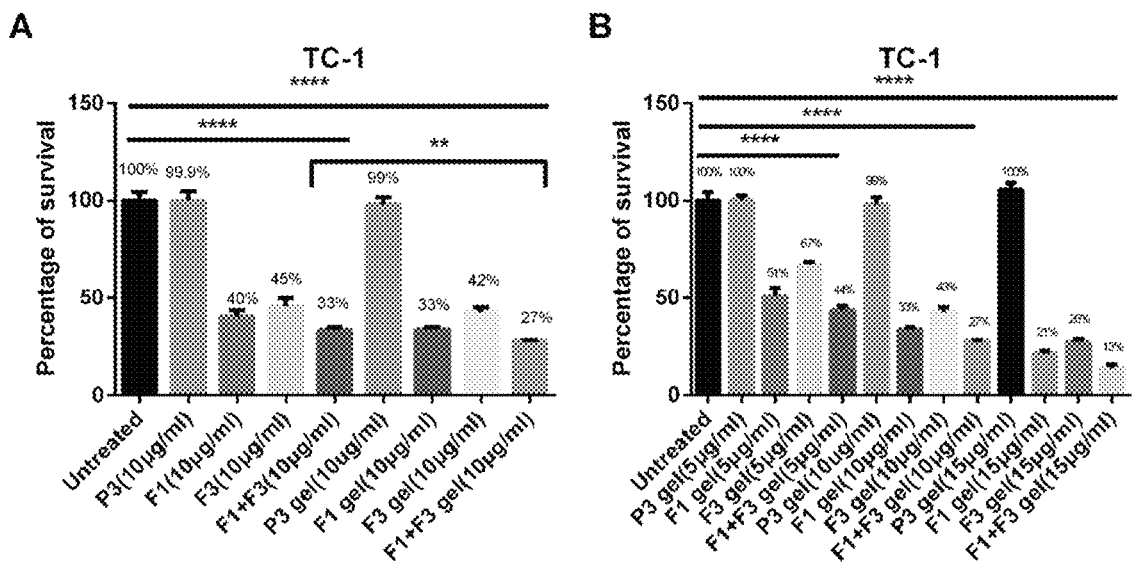
FIG. 20A and FIG. 20B are graphs illustrating survival rates of C57BL/6 mice inoculated with TC-1 cells and treated with P3 polypeptide, F1 polypeptide, F3 polypeptide, a mixture of F1 and F3, and gels thereof with different concentrations, wherein the gels had been prepared and stored for 30 days before using.
Figure 21A:
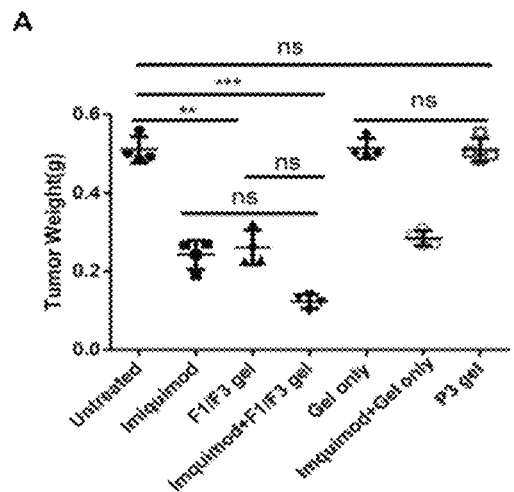
Figure 21B:
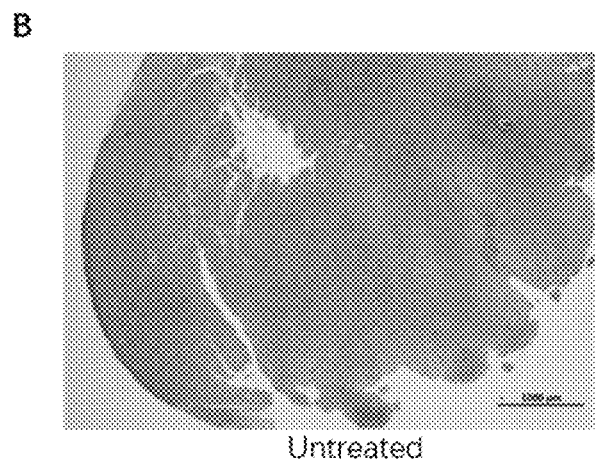
Figure 21C:
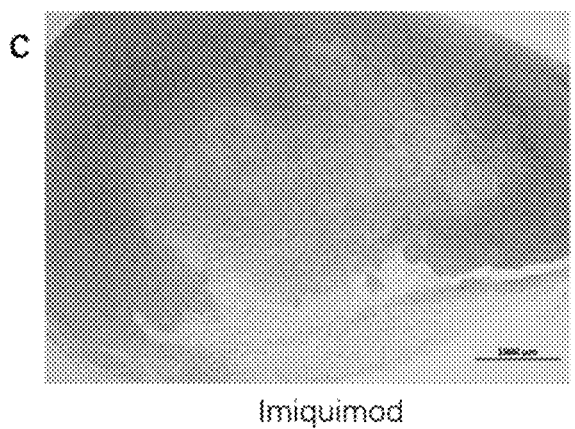
Figure 21D:
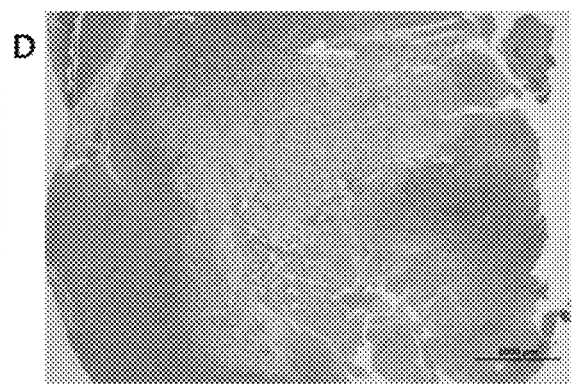

FIGS. 20A and 20B are graphs illustrating survival rates of C57BL/6 mice inoculated with TC-1 cells and treated with P3 polypeptide, F1 polypeptide, F3 polypeptide, a mixture of F1 and F3, and gels thereof with different concentrations in a MTT assay, wherein the gels had been prepared and stored for 30 days before using. It can be seen that the gel prepared by the F1 and/or F3 has high stability.

C57BL/6 mice were inoculated with TC-1 cells and treated with P3 polypeptide gel, 5% Imiquimod, a gel having no active component, a gel containing the F1 polypeptide and the F3 polypeptide, the gel having no active component in combination of 5% Imiquimod, and the gel containing the F1 polypeptide and the F3 polypeptide in combination of 5% Imiquimod after 4 days of inoculation. The results are shown in FIGS. 21A to 21H. It can be seen that the smear of the gel containing the F1 polypeptide and the F3 polypeptide can significantly inhibit the growth of tumor. The gel containing the F1 polypeptide and the F3 polypeptide in combination with 5% Imiquimod has best inhibiting effect on growth of tumor.

Figure 22A:
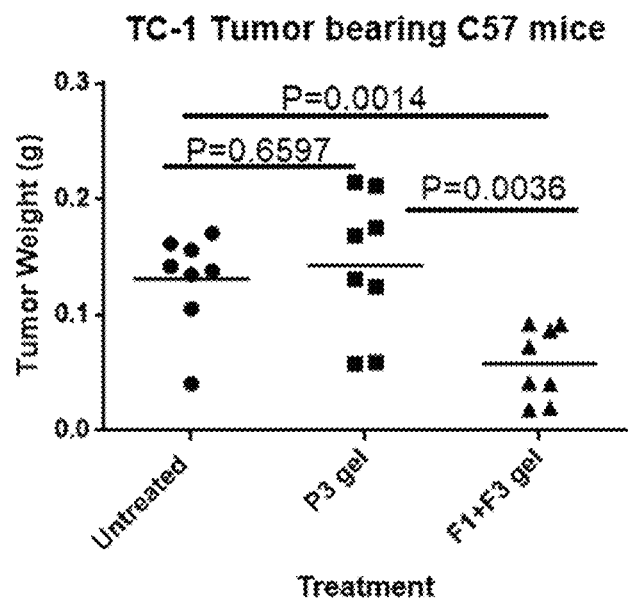
FIG. 22A is a graph illustrating weights of tumors of C57BL/6 mice inoculated with TC-1 cells and treated by PBS, P3 polypeptide gel, and a gel containing the F1 polypeptide and the F3 polypeptide.
Figure 22B:
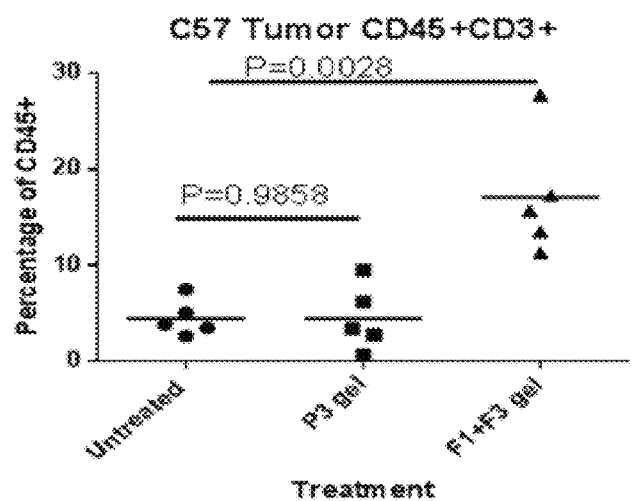
FIG. 22B and FIG. 22C are graphs illustrating infiltrations of CD3+T cells and NK cells into tissues of tumors of C57BL/6 mice inoculated with TC-1 cells and treated with PBS, P3 polypeptide gel, and a gel containing the F1 polypeptide and the F3 polypeptide.
Figure 22C:
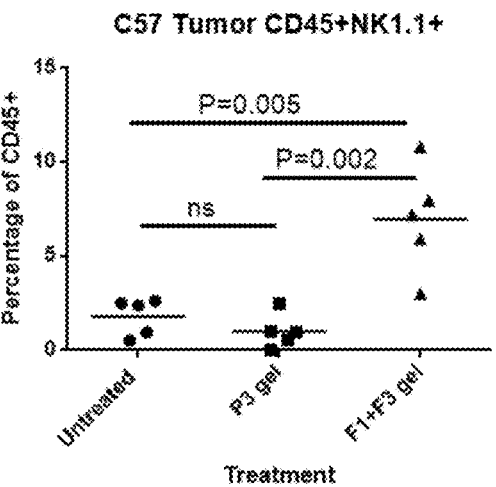
Figure 22D:
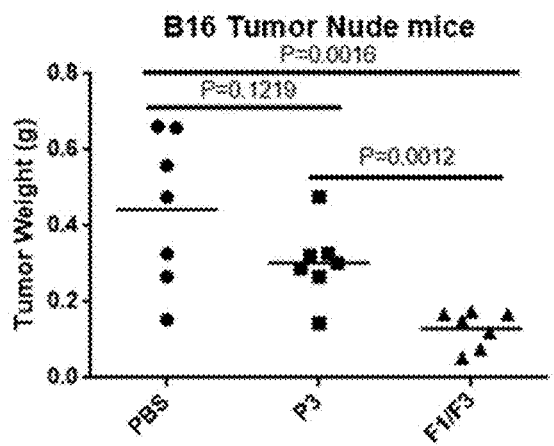
FIG. 22D is a graph illustrating weights of tumors of nude mice inoculated with B16 cells and treated with PBS, P3 polypeptide gel, and a gel containing the F1 polypeptide and the F3 polypeptide.
Figure 22E:
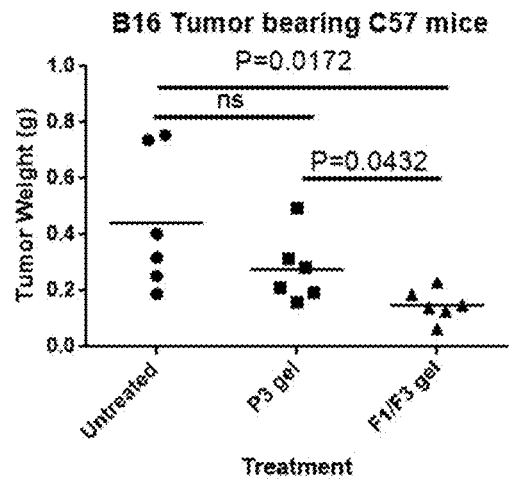
FIG. 22E is a graph illustrating weights of tumors of C57BL/6 mice inoculated with B16 cells and treated with PBS, P3 polypeptide gel, and a gel containing the F1 polypeptide and the F3 polypeptide.

FIG. 22A is a graph illustrating weights of tumors of C57BL/6 mice inoculated with TC-1 cells smeared with PBS, P3 polypeptide gel, and a gel containing the F1 polypeptide and the F3 polypeptide; FIGS. 22B and 22C are graphs illustrating infiltrations of CD3+T cells and NK cells into tissues of tumors of C57BL/6 mice inoculated with TC-1 cells smeared with PBS, P3 polypeptide gel, and a gel containing the F1 polypeptide and the F3 polypeptide. It can be seen that more T cells and NK cells were infiltrated into tumors C57BL/6 mice smeared with gel containing the F1 polypeptide and the F3 polypeptide than that of C57BL/6 mice smeared with PBS or P3 polypeptide gel. FIG. 22D is a graph illustrating weights of tumors of nude mice inoculated with B16 cells intra-tumor injected with PBS, P3 polypeptide, and the F1 polypeptide and the F3 polypeptide, showing that the F1 and F3 polypeptide also inhibit B16 cell growth of nude mice. FIG. 22E is a graph illustrating weights of tumors of C57BL/6 mice inoculated with B16 cells intra-tumor injected with PBS, P3 polypeptide, and the F1 polypeptide and the F3 polypeptide, showing that the F1 and F3 polypeptides inhibit B16 cell growth in C57BL/6 mice.

The present disclosure further provides a pharmaceutical composition including the F1 polypeptide and/or the F3 polypeptide. The pharmaceutical composition can be used in treating a disease associated with or not associated with a HPV infection. In one embodiment, the pharmaceutical composition can be used for treating a wart associated with the HPV infection, such as condyloma acuminate, verruca vulgaris, and verruca plana. In another embodiment, the pharmaceutical composition can be used for treating a solid tumor associated with the HPV infection, such as cervical cancer, vulvar cancer, penile cancer, and anal cancer, or not associated with the HPV infection, such as oral cancer, head and neck neoplasm, skin cancer, melanocytoma, etc. The pharmaceutical composition can be used for treating the disease in combination with a Toll like receptor agonist, such as Imiquimod, CpG, and a mixture thereof, or a therapeutic vaccine for tumor.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A pharmaceutical composition for treating a solid tumor or a disease associated with a HPV infection, comprising a F1 polypeptide, a F3 polypeptide, or a mixture thereof, and further comprising a Toll like receptor agonist, wherein the F1 polypeptide comprises SEQ ID NO: 1, and the F3 polypeptide comprises SEQ ID NO: 2.

2. The pharmaceutical composition of claim 1, wherein the pharmaceutical composition is prepared as an injection liquid suitable for parenteral administration or as an emulsion or an ointment suitable for percutaneous administration.

3. The pharmaceutical composition of claim 1, wherein a dose of the pharmaceutical composition comprises 3 µg to 30 µg of the F1 polypeptide, the F3 polypeptide, or a mixture thereof when used for tumor bearing mice.

4. The pharmaceutical composition of claim 1, wherein the Toll like receptor agonist is Imiquimod, CpG, or a mixture thereof.

5. The pharmaceutical composition of claim 1, further comprising a pharmaceutically acceptable excipient.

6. A method for treating a disease associated with a HPV infection, comprising administering to a subject in need thereof a pharmaceutical composition, wherein the pharmaceutical composition comprises a F1 polypeptide, a F3 polypeptide, or a mixture thereof and further comprises a Toll like receptor agonist, wherein the F1 polypeptide comprises SEQ ID NO: 1, and the F3 polypeptide comprises SEQ ID NO: 2.

7. The method of claim 6, wherein the disease is a wart.

8. The method of claim 7, wherein the disease is condyloma acuminate, verruca vulgaris, or verruca plana.

9. The method of claim 6, wherein the Toll like receptor agonist is Imiquimod, CpG, or a mixture thereof.

10. A method for treating a solid tumor, comprising administering to a subject in need thereof a pharmaceutical composition, wherein the pharmaceutical composition comprises a F1 polypeptide, a F3 polypeptide, or a mixture thereof and further comprises a Toll like receptor agonist, wherein the F1 polypeptide comprises SEQ ID NO: 1, and the F3 polypeptide comprises SEQ ID NO: 2.

11. The method of claim 10, wherein the solid tumor is cervical cancer, vulvar cancer, penile cancer, anal cancer, oral cancer, head and neck neoplasm, skin cancer, or melanocytoma.

12. The method of claim 10, wherein the Toll like receptor agonist is Imiquimod, CpG, or a mixture thereof.

13. The method of claim 10, wherein the pharmaceutical composition is administrated in combination with a therapeutic vaccine for the solid tumor.

* * * * *

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial sequence
<220> FEATURE:
<223> OTHER INFORMATION: the sequence is synthesized

<400> SEQUENCE: 1

Gly Leu Leu Ser Val Leu Gly Ser Val Ala Lys His Val Leu Pro His
1               5                   10                  15

Val Val Pro Val Ile Ala Glu His Leu
            20                  25

<210> SEQ ID NO 2
<211> LENGTH: 25
<212> TYPE: PRT
<213> ORGANISM: Artificial sequence
<220> FEATURE:
<223> OTHER INFORMATION: the sequence is synthesized

<400> SEQUENCE: 2

Gly Leu Phe Gly Val Leu Gly Ser Ile Ala Lys His Leu Leu Pro His
1               5                   10                  15

Val Val Pro Val Ile Ala Glu Lys Leu
            20                  25
```